United States Patent
Oishi

(10) Patent No.: US 9,741,111 B2
(45) Date of Patent: Aug. 22, 2017

(54) SUBJECT INFORMATION ACQUIRING DEVICE AND SUBJECT INFORMATION ACQUIRING METHOD

(75) Inventor: Takuji Oishi, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 210 days.

(21) Appl. No.: 13/991,506

(22) PCT Filed: Dec. 20, 2011

(86) PCT No.: PCT/JP2011/080146
§ 371 (c)(1),
(2), (4) Date: Jun. 4, 2013

(87) PCT Pub. No.: WO2012/086842
PCT Pub. Date: Jun. 28, 2012

(65) Prior Publication Data
US 2013/0261427 A1    Oct. 3, 2013

(30) Foreign Application Priority Data

Dec. 24, 2010  (JP) ................................ 2010-288685

(51) Int. Cl.
*A61B 5/05* (2006.01)
*G06T 7/00* (2017.01)
(Continued)

(52) U.S. Cl.
CPC .......... *G06T 7/0012* (2013.01); *A61B 5/0095* (2013.01); *A61B 8/5269* (2013.01); *G01S 15/8977* (2013.01); *A61B 8/13* (2013.01)

(58) Field of Classification Search
CPC ... A61B 5/0095; A61B 5/0097; A61B 8/5269; G06T 7/0012; G01S 15/8977
(Continued)

(56) References Cited

U.S. PATENT DOCUMENTS 6,216,025 B1   4/2001  Kruger
7,353,054 B2   4/2008  Kawasaki et al.
(Continued)

FOREIGN PATENT DOCUMENTS

CN    1541622 A    11/2004
CN    101151550 A   3/2008
(Continued)

OTHER PUBLICATIONS

Office Action issued in Chinese Patent Application No. 201180061695.9, dated Jul. 3, 2014 (10 pages).
(Continued)

*Primary Examiner* — Rajeev Siripurapu
(74) *Attorney, Agent, or Firm* — Fitzpatrick, Cella, Harper & Scinto

(57) ABSTRACT

A subject information acquiring device has: an acoustic detector which receives an acoustic wave propagated in a subject and converts into an electrical signal; and a data processing device which generates a subject information distribution using the electrical signal, and the data processing device has a matching processing unit which acquires a similarity distribution by calculating a similarity between: template data indicating a relationship between a real image; and an artifact and the subject information distribution used as a matching information distribution, so that it is possible to provide a photoacoustic image forming diagnosing device which can distinguish between an image and a background even when the contrast is poor.

21 Claims, 16 Drawing Sheets

(51) Int. Cl.
 *A61B 5/00* (2006.01)
 *A61B 8/08* (2006.01)
 *G01S 15/89* (2006.01)
 *A61B 8/13* (2006.01)

(58) Field of Classification Search
 USPC ........................................................ 600/407
 See application file for complete search history.

(56) References Cited

U.S. PATENT DOCUMENTS

| | | | |
|---|---|---|---|
| 7,666,140 B2 | 2/2010 | Kato | |
| 7,740,585 B2 | 6/2010 | Oraevsky et al. | |
| 2002/0138005 A1 | 9/2002 | Ogawa | |
| 2004/0193053 A1 | 9/2004 | Kato | |
| 2006/0235302 A1* | 10/2006 | Grossman | A61B 8/08 600/443 |
| 2007/0055118 A1 | 3/2007 | Kawasaki et al. | |
| 2007/0078316 A1 | 4/2007 | Hoarau et al. | |
| 2008/0166016 A1 | 7/2008 | Sibiryakov et al. | |
| 2009/0002685 A1* | 1/2009 | Fukutani et al. | 356/72 |
| 2009/0043216 A1 | 2/2009 | Lin et al. | |
| 2010/0081903 A1 | 4/2010 | Izzetoglu | |
| 2010/0087733 A1 | 4/2010 | Nakajima et al. | |
| 2010/0150412 A1 | 6/2010 | Robinson | |
| 2010/0191109 A1 | 7/2010 | Fukutani et al. | |
| 2010/0268042 A1* | 10/2010 | Wang | A61B 5/0059 600/322 |
| 2011/0178385 A1 | 7/2011 | Fukutani et al. | |

FOREIGN PATENT DOCUMENTS

| | | |
|---|---|---|
| EP | 1665985 A1 | 6/2006 |
| JP | 2002-536041 A | 10/2002 |
| JP | 2008-530700 A | 8/2008 |
| JP | 2010-35806 A | 2/2010 |
| JP | 2010-88497 A | 4/2010 |
| WO | 20101024290 A1 | 3/2010 |
| WO | WO 2010027095 A1 * | 3/2010 |

OTHER PUBLICATIONS

X. Wang et al., "Noninvasive Imaging of Hemoglobin Concentration and Oxygenation in the Rat Brain Using High-Resolution Photoacoustic Tomography", *Journal of Biomedical Optics* 11(2), 024015 (Mar./Apr. 2006).

Y. Xu et al., "Signal Processing in Scanning Thermoacousitc Tomography in Biological Tissues", *Medical Physics*, vol. 28, No. 7 XP012011531 (Jul. 1, 2001).

L. Jiang et al., "Sinogram Restoration for Ultra-Low-Dose X-Ray Multi-Slice Helical CT by Nonparametric Regression", *Proceedings of SPIE*, vol. 6510 XP55005664 (Jan. 1, 2007).

I. Patrickeyev et al., "Removing Image Artifacts in Optoacousitc Tomography Using Virtual Transducer Restoration", *Proceedings of the SPIE*, vol. 5320, pp. 249-256 XP040255188 (2004).

Office action dated Sep. 24, 2015, in corresponding Japanese Patent Application No. 2011-273233 (7 pages including translation).

* cited by examiner

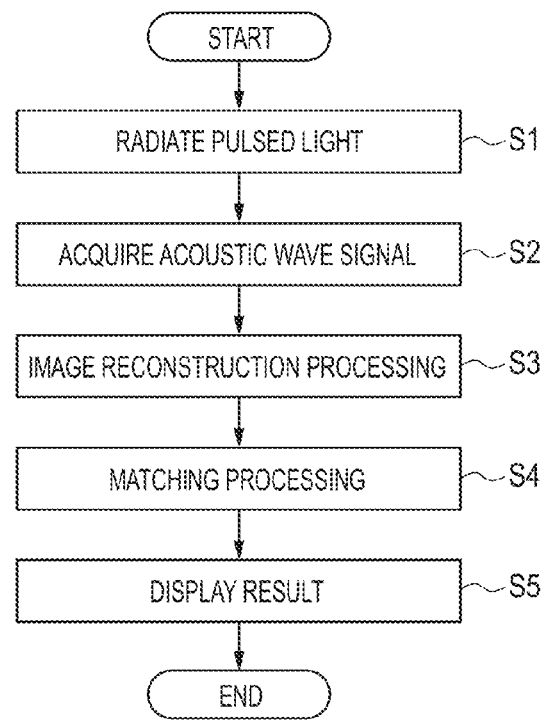
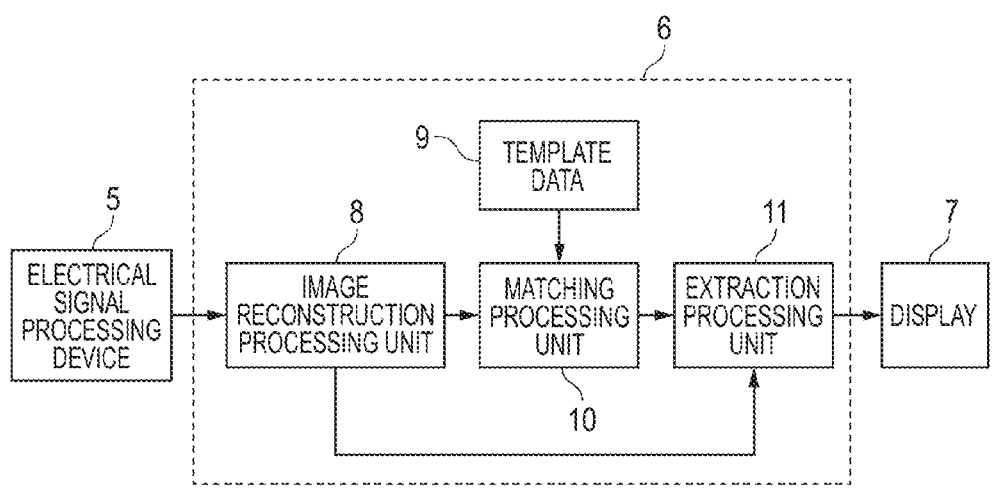

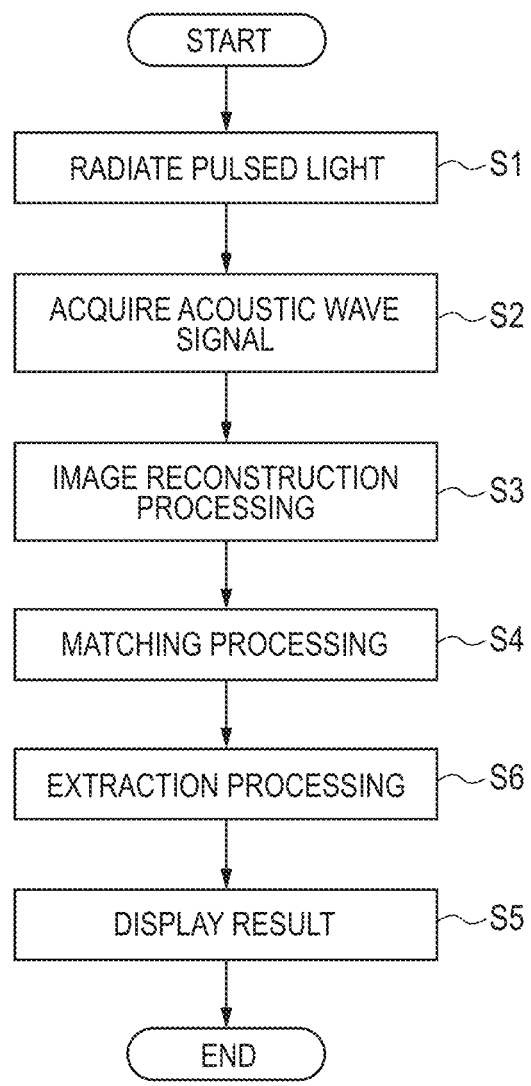

SUBJECT INFORMATION ACQUIRING DEVICE AND SUBJECT INFORMATION ACQUIRING METHOD

TECHNICAL FIELD

The present invention relates to a subject information acquiring method and a subject information acquiring method. More particularly, the present invention relates to a technique utilizing a photoacoustic effect or a technique utilizing an ultrasound echo.

BACKGROUND ART

Subject information acquiring devices which use X rays and ultrasounds are used in many fields which require nondestructive test, including a medical field. In the field of subject information acquiring devices in the medical, physiological information (that is, function information) about a biological body can be effectively used to find an ailing site such as cancer, and thus imaging of function information has been studied in recent years. A photoacoustic tomography (PAT) which is one of optical imaging techniques is proposed as one of diagnosing methods using function information. While X-ray diagnosis or ultrasound diagnosis can only acquire morphology information about the interior of the biological body, the photoacoustic tomography can acquire both of morphology and function information with non-invasive diagnosis.

In The photoacoustic tomography, pulsed light produced from a light source is radiated on an interior of a subject, and then an acoustic wave (typically, ultrasound) produced by a photoacoustic effect of internal tissues which absorbed light propagated and diffused in the subject is detected. The detected acoustic wave which contains information about the internal tissues which is the source of the acoustic wave is then converted into an image of the information. By detecting a temporal change of the received acoustic wave at a plurality of sites encircling the subject, and mathematically analyzing (reconstructing) the obtained signal, it is possible to three-dimensionally visualize information related to an optical characteristic value inside the subject. This information can be used as morphology information about the interior of the subject, and, further, function information including an optical characteristic value distribution such as an absorption coefficient distribution inside the subject can also be obtained from the initial acoustic pressure distribution produced by radiating light on the interior of the subject.

As the pulsed light to be radiated on the interior of the subject near-infrared light, for example, can be used. Near-infrared light has the property that it easily transmits through water which constitutes most part of the biological body, while it is easily absorbed by hemoglobin in blood, so that it is possible to image a blood vessel image as morphology information. Further, by using the absorption coefficient distribution obtained by radiating near-infrared light, it is possible to learn a content rate of oxygenated hemoglobin to all hemoglobin in blood, that is, it is possible to learn the oxygen saturation and, consequently, imaging of biological function can also be performed. The oxygen saturation distribution serves as an indicator to distinguish whether a tumor is benign or malignant, and hence photoacoustic tomography is expected as a way for efficiently finding malignant tumors.

The oxygen saturation is calculated by performing a plurality times of measurements using pulsed light of different wavelengths, and then performing a comparison operation of calculating the ratio of absorption coefficients calculated for different wavelengths. This is based on a principle that optical absorption spectra of deoxygenated hemoglobin and oxygenated hemoglobin are different. The content rate can be consequently found out by measuring and comparing the spectra according to the different wavelengths.

In those imaging processes, when the obtained absorption coefficients are directly used for the comparison operation of calculating the ratio, a blood vessel image portion and a background portion cannot be distinguished, and therefore, as disclosed in Non Patent Literature 1, it is necessary to distinguish between the blood vessel image portion and background portion and process only the blood vessel image portion.

CITATION LIST

Non Patent Literature

NPL 1: Xueding Wang, et al. "Noninvasive imaging of hemoglobin concentration and oxygenation in the rat brain using high-resolution photoacoustic tomography" Journal of Biomedical Optics 11(2), 024015 (March/April 2006)

SUMMARY OF INVENTION

Technical Problem

Conventionally, a real image portion such as a blood vessel image and a background portion are distinguished by using a threshold method of providing a threshold with respect to a voxel value of the optical characteristic value distribution, such as an absorption coefficient distribution, and deciding the voxel having a voxel value equal to or more than the threshold as the real image portion. However, there is a problem that, when a contrast is poor between the real image portion and background portion, this method cannot distinguish between the real image portion and background portion well. When the contrast is poor in the optical characteristic value distribution, that is, when noise of the background portion is significant and a voxel value of the background portion is equal to or greater than the real image portion, the threshold method of setting the threshold with respect to the voxel value could not be useful for distinguishing between the background portion and real image portion. This problem is not only related to the threshold method, but all methods of distinguishing between a background portion and a real image portion utilizing voxel values can be suffered from similar problem. In particular, since the contrast deteriorates at the depth of the biological body, it is difficult to distinguish between the real image portion and background portion at the depth of the biological body.

The present invention is made based on this recognition of the problem. It is therefore an object of the present invention to provide a subject information acquiring device and a subject information acquiring method which can distinguish between a real image and a background even when the contrast is poor.

Solution to Problem

In light of the above problem, a subject information acquiring device has: an acoustic detector which receives an acoustic wave propagated in a subject and converts into an electrical signal; and a data processing device which generates a subject information distribution using the electrical signal, and the data processing device has a matching processing unit which acquires a similarity distribution by calculating a similarity between: template data indicating a relationship between a real image and an artifact; and the subject information distribution which is a matching information distribution.

Advantageous Effects of Invention

According to the present invention, it is possible to distinguish between a real image and background even when the contrast is poor.

Further features of the present invention will become apparent from the following description of exemplary embodiments with reference to the attached drawings.

BRIEF DESCRIPTION OF DRAWINGS

FIG. 4 is a flowchart illustrating an operation of the device according to an embodiment of the present invention.

FIG. 5 is a schematic diagram illustrating the configuration of the device according to an embodiment of the present invention.

FIG. 6 is a flowchart illustrating an operation of the device according to an embodiment of the present invention.

DESCRIPTION OF EMBODIMENTS

Hereinafter, the present invention will be described using the drawings. In the present invention, an acoustic wave typically is an ultrasound, while it includes elastic waves referred to as a sound wave, ultrasound, acoustic wave, photoacoustic wave and photo ultrasound. An acoustic wave detector receives an acoustic wave which has been produced or reflected in a subject and propagated in the subject. A subject information acquiring device according to the present invention includes a device which utilizes an ultrasound echo technique of transmitting an ultrasound to the subject, receiving a reflected wave (reflected ultrasound) reflected inside the subject and acquiring a subject information distribution as image data, or a device which utilizes a photoacoustic effect of radiating light (electromagnetic wave) on the subject, receiving an acoustic wave (typically, ultrasound) produced in the subject and acquiring the subject information distribution as image data. In case of the former device utilizing the ultrasound echo technique, subject information to be acquired reflects differences of acoustic impedances of tissues inside the subject. In case of the latter device utilizing the photoacoustic effect, subject information to be acquired includes an acoustic wave source distribution produced by radiation of light, initial acoustic pressure distribution in the subject, optical energy absorption density distribution derived from the initial acoustic pressure distribution, absorption coefficient distribution and concentration information distribution of substances constituting tissues. The concentration information distribution of substances is, for example, an oxygen saturation distribution, or oxy and deoxy hemoglobin concentration distribution concentration distributions.

In the following embodiments, the present invention will be described using a photoacoustic device based on the photoacoustic tomography (PAT) of generating one or more types of subject information distributions by radiating light on the interior of the subject and receiving, at an acoustic wave detector, a photoacoustic wave excited inside the subject. However, the present invention is by no means limited to these embodiments, and the present invention is also applicable to any subject information acquiring devices as long as they can distinguish between a real image and artifacts by measuring a similarity with a template. Further, the present invention is by no means limited only to a single device, and the present invention also incorporates a method of distinguishing a real image and artifacts described in the following embodiments, and a program of executing this method. A real image refers to an image in which, when the real image is converted into an image, an optical absorber having a great optical absorption coefficient in the subject appears as an image.

[Basic Embodiment]

Figure 1:
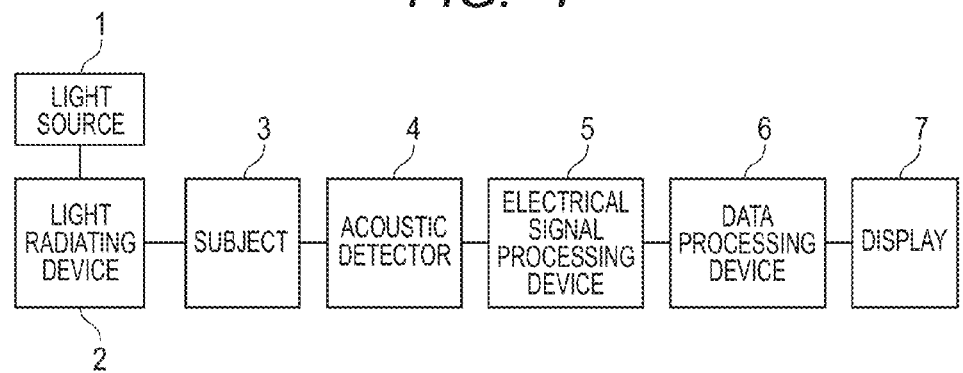
FIG. 1 is a schematic diagram illustrating a configuration of the device according to an embodiment of the present invention.

The present invention distinguishes between an image and background by utilizing a certain relationship between a real image and artifacts (virtual image). The basic embodiment for implementing this distinction is as follows. In FIG. 1, a light source 1, a light radiating device 2, a subject 3, an acoustic detector 4, an electrical signal processing device 5, a data processing device 6 and a display 7 according to the present embodiment is illustrated.

(Light Source)

The light source 1 is a device which produces pulsed light. The light source is preferably a laser to obtain a great output, or the light source may also be a light emitting diode. To effectively produce a photoacoustic wave, it is necessary to radiate light for a sufficiently short time according to thermal characteristics of the subject. In the present embodiment, a biological body is assumed as the subject, and the pulse width of pulsed light produced from the light source 1 is preferably several tens of nanoseconds or less. Further, the wavelength of pulsed light is preferably in the near-infrared area of about 500 nm to 1200 nm which is referred to as the biological window. Light in this area can comparatively reach the depth of the biological body, and hence it is useful in obtaining information about the depth. The wavelength of pulsed light preferably has a larger absorption coefficient with respect to an observation target.

(Light Radiating Device)

The light radiating device 2 guides pulsed light, produced in the light source 1, to the subject 3. More specifically, the light radiating device 2 includes optical equipment such as an optical fiber, lens, mirror and diffuser plate. Further, by using this optical equipment, it is possible to change the shape and optical density of the guided pulsed light. The optical equipment is by no means limited to the ones described herein, and may be any equipment as long as it satisfies these functions.

(Subject)

The subject 3 is a measurement target. For the subject, it is possible to use a biological body or a phantom which simulates acoustic characteristics and optical characteristics of a biological body. The acoustic characteristics specifically refer to a propagation speed and attenuation rate of the acoustic wave, and the optical characteristics specifically refer to an absorption coefficient and scattering coefficient of light. An optical absorber having a great absorption coefficient is necessarily be present inside the subject. In case of the biological body, the optical absorber specifically includes, for example, hemoglobin, water, melanin, collagen and fat. In case of the phantom, substances which simulate the above optical characteristics are sealed inside as the optical absorber.

(Acoustic Detector)

The acoustic detector 4 is acoustically coupled to the subject, and it receives and the acoustic wave which is excited when the optical absorber absorbs part of energy of radiated pulsed light, and converts into an electrical signal (received signal). According to the photoacoustic tomography, the acoustic wave needs to be captured at a plurality of sites, and therefore it is preferable to use a 2D type which aligns a plurality of acoustic detecting elements on a planar surface. It may be, however, possible to capture the acoustic wave by using a 1D type which aligns acoustic detecting elements in a row or a single acoustic detecting element, to a plurality of sites by moving with means of a scanning device. The acoustic detector preferably has a high sensitivity and wider frequency band and, more specifically, such as an acoustic detector using a piezoelectric lead-zirconate-titanate (PZT), polyvinylidene fluoride (PVDF), capacitive micromachined ultrasonic transducer (cMUT) or Fabry-Perot interferometer. However, the acoustic detector is not limited to the acoustic detector described herein, and any acoustic detectors as long as they can satisfy the function of capturing the acoustic wave may be used.

(Electrical Signal Processing Device)

The electrical signal processing device 5 amplifies an analog electrical signal obtained in the acoustic detector 4, and converts the analog electrical signal into a digital signal. The same number of analog-digital converters (ADCs) equal to the number of acoustic detectors is preferably provided to efficiently acquire data, or one ADC may be sequentially changed, reconnected and used.

(Data Processing Device)

The data processing device 6 acquires the subject information distribution as image data by processing the digital signal (received digital signal) obtained in the electrical signal processing device 5. The feature of the present invention lies in processing performed in this data processing device. More specifically, the data processing device includes, for example, a computer or an electrical circuit.

(Display)

The display 7 displays image data generated in the data processing device 6 as an image. More specifically, the display 7 is a display of a computer or television.

(Internal Configuration of Data Processing Device)

Figure 2:
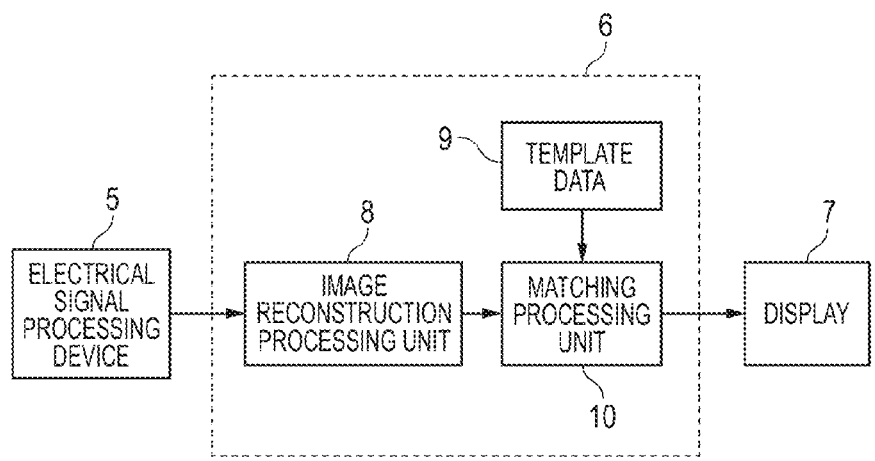
FIG. 2 is a schematic diagram illustrating a configuration of the device according to an embodiment of the present invention.

The internal configuration of the data processing device 6 is as follows. As illustrated in FIG. 2, the data processing device 6 is formed with an image reconstruction processing unit 8, a template data holding unit which holds template data 9 and a matching processing unit 10. The image reconstruction processing unit 8 filters the digital signal obtained at each position and back-projects the digital signal at each position, and thus it acquires a subject information distribution such as an initial acoustic pressure distribution indicating the position of the acoustic source in pixel or voxel data. As will be described below, the template data 9 is the subject information distribution such as the initial acoustic pressure distribution which serves as a template indicating the relationship between a real image and artifacts appear nearby back and forth of the real image or appeared rearward the real image. As will be described below, the matching processing unit 10 acquires a similarity distribution by calculating a similarity between template data and the subject information distribution such as the initial acoustic pressure distribution.

Figure 17A:
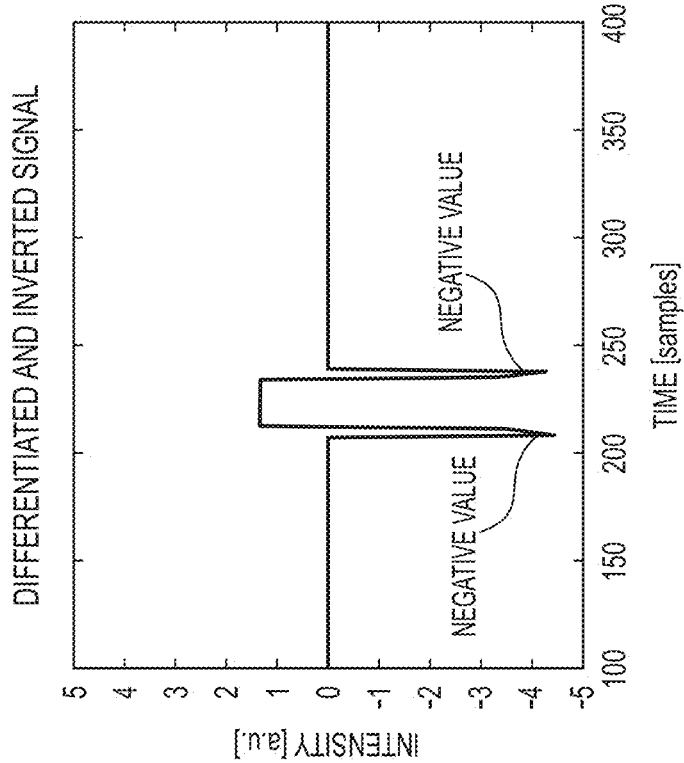
FIG. 17A is an original signal used in back projection.
Figure 17B:
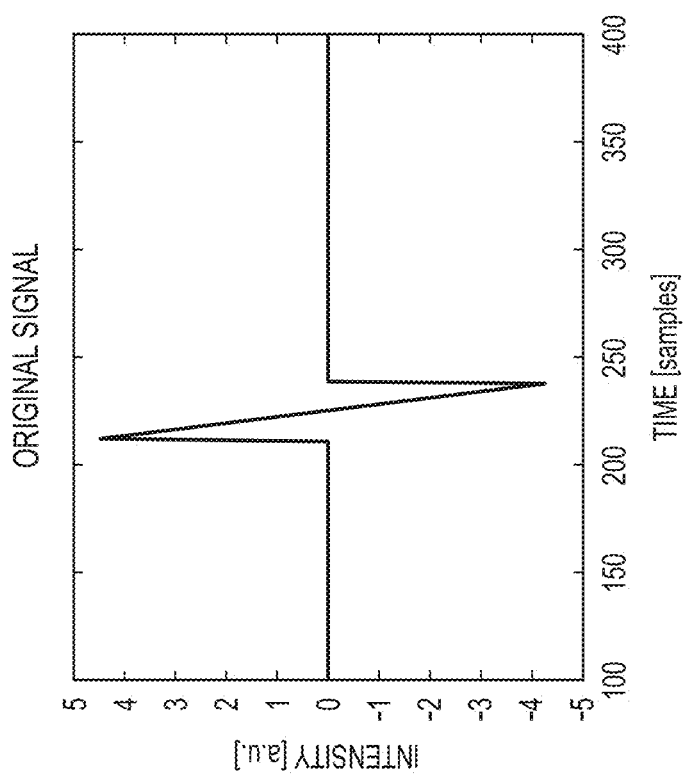
FIG. 17B is a differentiated and inverted signal used in back projection.

The principle of the template data 9 and processing in the matching processing unit 10 which is the gist of the present invention will be described. Back projection performed in the image reconstruction processing unit 8 is a method which is also called universal back projection. In the method, first, an original signal (FIG. 17A) detected by the detector is differentiated and the negative and positive values are inverted (FIG. 17B). As is illustrated in FIG. 17B, two negative peaks appear after the processes. Then, concentric spheres which concentrate around the position of the detector are drawn in a three-dimensional space in proportion to the inverted value. When the above process is conducted for a plurality of detectors and thus obtained data are composed to generate voxel data, the initial acoustic source position can be obtained. However, an artifact (also referred to as "ghost") which is a shadow which does not originally exist may be appeared by the composition performed upon back projection.

Figure 3A:
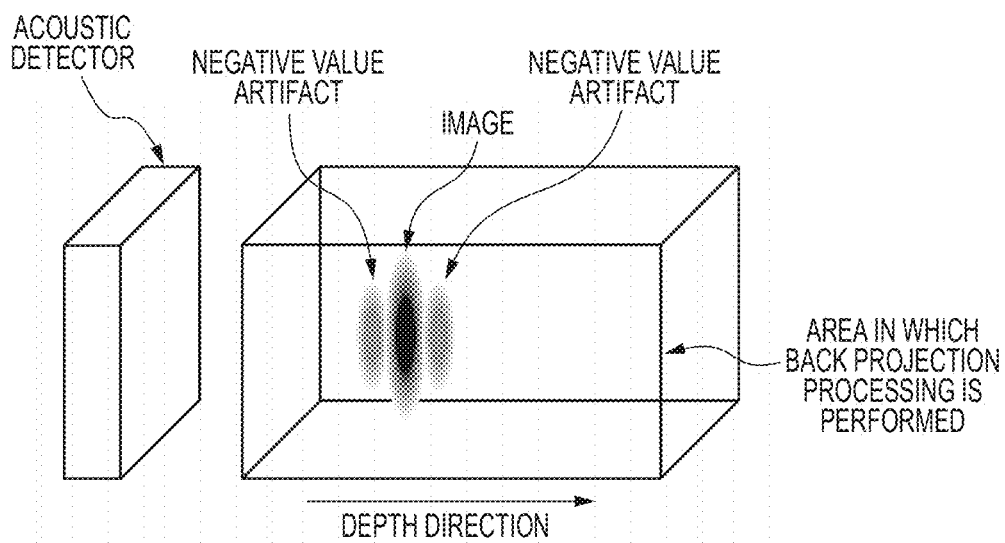
FIG. 3A is a view illustrating the relationship between a real image and negative artifacts.

When the acoustic detectors are arranged to spherically encircle the subject, the portion other than the original image is completely canceled and only a real image is left upon composition performed in back projection, and the problem due to the artifact may not occur. However, when the arrangement of the detectors is planar and only a part of acoustic wave propagated in a specific direction, among whole generated acoustic waves, is detected, cancellation becomes incomplete. Therefore the negative artifacts due to the negative values of FIG. 17B may appear in back and forth directions seen from the acoustic detector, as illustrated in FIG. 3A, of the real image.

Figure 3B:
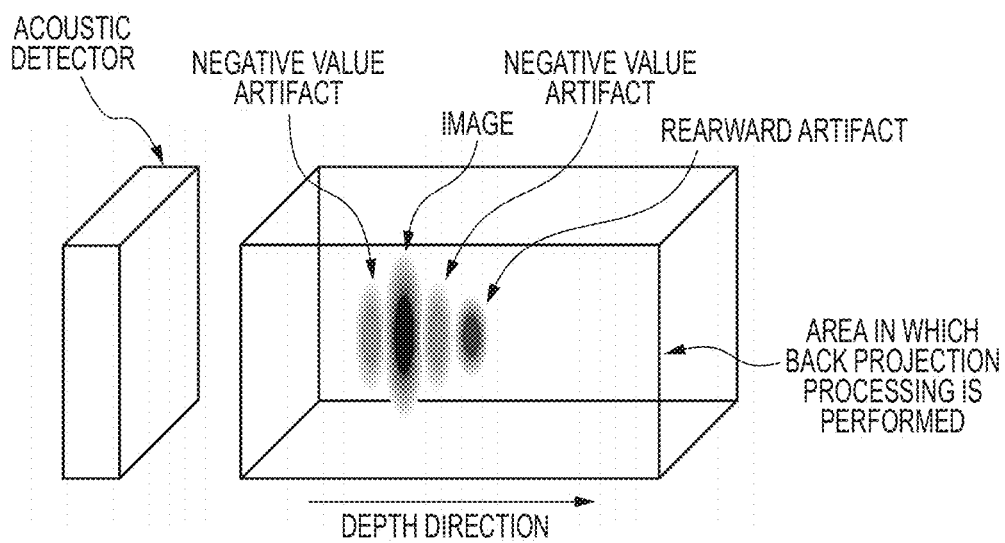
FIG. 3B is a view illustrating the relationship between a real image and a rearward artifact.
Figure 18A:
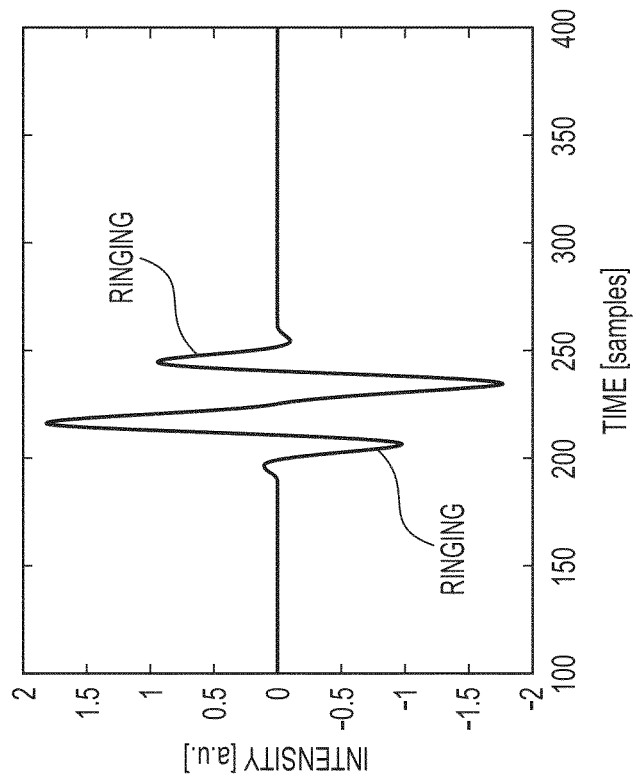
FIG. 18A is a signal obtained when the whole frequency bands are detected.
Figure 18B:
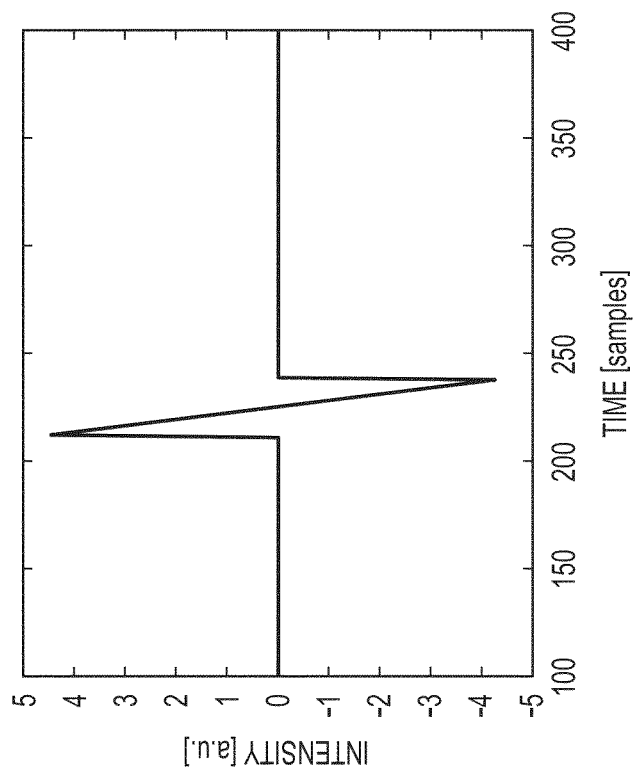
FIG. 18B is a signal obtained when a limited frequency bands are detected.

On the other hand, response characteristics of the acoustic detector may also cause an artifact. When the frequency band of the acoustic detectors is not limited, the detector can detect whole frequency bands to obtain signals as represented in FIG. 18A. When, conversely, the frequency band of the acoustic detectors is limited, signals cannot be completely reproduced and the acoustic detector's response varies dependent on the frequency band, which results in obtaining signals including ringing, as illustrated in FIG. 18B. This ringing causes an artifact when back projection is performed. Specifically, it causes an artifact (referred in this specifications to as a rearward artifact, also called a ringing artifact) appeared farther rearward (a far position seen from the acoustic detector), seen form the acoustic detector side, as illustrated in FIG. 3B, of the negative artifacts positioned back and forth of a real image.

In this case, since the negative artifacts appeared back and forth of the real image is due to rising and falling of the signal, the negative artifacts appear nearby the real image. Similarly, the intensity ratio of the real image and the negative artifacts, as well as the ratio (dimension ratio) of the sizes of the real image and the negative artifacts, would be approximately the same.

Further, the following relationship is seen between the real image and the rearward artifact. That is, the distance between the real image and the rearward artifact is determined according to a time lag between the signal and ringing, which distance being constant if the acoustic detectors are the same. In addition, the intensity ratio of the real image and the rearward artifact is determined according to the intensity ratio of the signal and ringing. This ringing intensity changes depending on frequency components of the signal. Since the frequency components of the signal generated due to the photoacoustic effect depend on the size of the optical absorber, the intensity ratio of the real image and the rearward artifact depends on the size of the optical absorber and, when the size of the optical absorber is constant, the intensity ratio also becomes constant. Further, the dimension ratio of the real image and the rearward artifact is also determined according to the widths of the signal and ringing wave. Since the width of the signal generated due to the photoacoustic effect depends on the size of the optical absorber, the dimension ratio of the real image and the rearward artifact depends on the size of the optical absorber and, when the size of the optical absorber is constant, the dimension ratio is almost constant. As described above, when a given image is a real image resulting from the photoacoustic signal produced by the absorption coefficient difference in the subject, this image is accompanied by artifacts appeared nearby back and forth of the real image or appeared rearward the real image having a certain relationship with the real image. Conversely, when the image is produced by an artifact or noise, there are no artifacts having the above certain relationship with this image. Consequently, by checking the relationship between the image and artifact appeared nearby back and forth or rearward of the image per acoustic detector, it is possible to decide whether or not this image is a real image. Especially when the rearward background due to ringing appears, since more information can be used for discrimination compared to a case when only negative artifacts appeared back and forth of the image are used, whether or not the image is a real image can be distinguished more accurately.

The method of implementing the above principle will be described using FIGS. 1, 2 and 4. The light source 1 produces pulsed light, and the light radiating device 2 radiates the pulsed light on the subject (S1). The acoustic wave detector 4 and electrical signal processing device 5 acquire the acoustic wave produced from the subject 3 by radiating the pulsed light on the subject 3 (S2). The image reconstruction processing unit 8 reconstructs the obtained signals sequentially (S3).

The template data 9 is obtained from a received signal such as the initial acoustic pressure distribution taking into account the position where the acoustic detector used for measurement is positioned or the response characteristics such as frequency characteristics of the acoustic detector, and it indicates the relationship between a real image and negative artifacts or rearwards artifact of this real image. The relationship between this real image and artifact means at least one of a distance between the real image and the artifact, the intensity ratio of the real image and artifact and the dimension ratio of the real image and artifact among the subject information distribution obtained by receiving the acoustic wave signal from the subject. The template data preferably includes all of the distance, intensity ratio and dimension ratio of the real image and artifact. However, the present invention can be implemented only if at least one of the above three relationships (distance, intensity ratio and dimension ratio) is included in the template data. While the initial acoustic pressure distribution is used for the subject information distribution in the present embodiment, the optical characteristic distribution such as the absorption coefficient distribution may be used as described in the other embodiments. The response characteristics of the acoustic detector mean unique characteristics of each acoustic detector, which are likely to influence the relationship between the real image and artifact of the real image, and include, for example, the size of the detection face as well as frequency band characteristics. In the present invention, the subject information distribution includes "a matching information distribution" that is a distribution used as a target for matching processing, and "an extraction information distribution" that is a distribution used as a target for extraction processing. As will be described in each following embodiment, the same type of the subject information distribution may be used or different types of subject information distributions may be used for the matching information distribution and extraction information distribution. The types of subject information distributions used for these pieces of information can be adequately selected according to the purpose of measurement.

The template data is preferably created by simulating measurement of a spherical optical absorber based on simulation in which the frequency band characteristics of the acoustic detector is taken into account. However, the shape of the optical absorber used for simulation may have a shape other than the spherical shape, and otherwise the template data may be created by actual measurement. When data obtained from measurement includes a given image and an image which is assumed to be an artifact of the image, and the data is similar to this template data, it may be said that the relationship between this image and the image which is assumed to be an artifact of this image is similar to the relationship between the real image and the artifact of the real image, and this data is highly likely to include a real image. The matching processing unit 10 extracts voxel data having the same size as the template data 9 from a given position in the initial acoustic pressure distribution obtained by the image reconstruction processing unit 8, and calculates the similarity between the extracted data and the template data 9. The initial acoustic pressure distribution used upon this matching processing is used for a matching information distribution. Further, the matching processing unit 10 calculates the similarity likewise by moving the position to extract the initial acoustic pressure distribution, and creates the similarity distribution by repeating this calculation (S4). The similarity distribution is a three-dimensional new subject information distribution which represents the similarities of template data with respect to voxels of the initial acoustic pressure distribution. Although a similarity R is preferably calculated by zero-mean normalized cross-correlation (ZNCC) Equation 1 represented below, methods such as Sum of Squared Difference (SSD) or Sum of Absolute Difference (SAD) of calculating parameters indicating the similarity may be adopted.

$$R = \frac{\sum_{k=0}^{N-1}\sum_{j=0}^{M-1}\sum_{i=0}^{L-1}((I(i,j,k)-\bar{I})(T(i,j,k)-\bar{T}))}{\sqrt{\sum_{k=0}^{N-1}\sum_{j=0}^{M-1}\sum_{i=0}^{L-1}(I(i,j,k)-\bar{I})^2 \times \sum_{k=0}^{N-1}\sum_{j=0}^{M-1}\sum_{i=0}^{L-1}(T(i,j,k)-\bar{T})^2}}$$

Equation 1

Meanwhile, L, M and N respectively refer to the numbers of voxels in a X direction, Y direction and Z direction in the XYZ coordinate, and I (i, j, k) refers to a distribution extracted from the initial acoustic pressure distribution obtained by the image reconstruction processing unit 8, $\bar{I}$ refers to an average value of the extracted distribution, and T (i, j, k) refers to template data, and $\bar{T}$ refers to an average value of template data. The display 7 displays the finally obtained similarity distribution (S5). By so doing, it is possible to display on the display unit which one of the initial acoustic pressure distributions is a real image, and distinguish between the real image and background.

[Second Embodiment]

Hereinafter, an embodiment will be described where processing of extracting a real image is performed utilizing the similarity distribution obtained in [Basic Embodiment]. The entire device configuration is the same as in [Basic Embodiment] and the implementing method is also the same up to S4 for creating the similarity distribution, and therefore differences will be described.

FIG. 5 illustrates an internal configuration of a data processing device 6, where an extraction processing unit 11 is arranged in addition to an image reconstruction processing unit 8, a template data 9 and a matching processing unit 10. The extraction processing unit 11 selects a voxel having a high similarity in the similarity distribution, and extracts only the initial acoustic pressure distribution of this voxel. In the present embodiment, the initial acoustic pressure distribution used for this extraction processing is used for the extraction information distribution. More specifically, this processing is directed to providing an arbitrary threshold with respect to similarity distributions, deciding whether the similarity distributions of the respective voxels are higher or smaller than the threshold, keeping only the voxels of the initial acoustic pressure distribution (the initial acoustic pressure distribution as the extraction information distribution) corresponding to the positions of the voxels having a higher similarity than the threshold, and rewriting the other voxel values of the initial acoustic pressure distribution (the initial acoustic pressure distribution as the extraction information distribution) to a value such as zero or minus which can be decided as error values. While such extracting method is desirable, a method is possible which, instead of assigning an error value to a voxel having a lower similarity, only reduces an acoustic pressure value of a voxel value to, for example, one tenth.

As illustrated in FIG. 6, according to the implementing method, matching processing (S4) is performed, extraction processing (S6) is then performed, and extracted data is displayed on the display 7 as a new subject information distribution (S5).

In the present embodiment, by displaying only the initial acoustic pressure distribution of the image portion, it is possible to substantially reduce the background portion and improve the contrast of the image.

[Third Embodiment]

Instead of calculating the similarity distribution using the initial acoustic pressure distribution and extracting the initial acoustic pressure distribution as in [Basic Embodiment] and [Second Embodiment], an embodiment will be described where the absorption coefficient distribution is used to calculate and extract a similarity distribution.

A photoacoustic diagnosing device can calculate an absorption coefficient distribution from an initial acoustic pressure distribution. A produced acoustic pressure P to be measured is represented by Equation 2.

$$P = \Gamma \cdot \mu_a \cdot \phi$$

Equation 2

Meanwhile, $\Gamma$ refers to a Grueneisen constant of the optical absorber, $\mu_a$ refers to the absorption coefficient of the optical absorber and $\phi$ refers to the amount of light which has reached the optical absorber. Since the Grueneisen constant can be regarded to be constant, the produced acoustic pressure is proportional to the product of the absorption coefficient and light amount. The light amount can be obtained by calculating propagation of light inside the biological body from the distribution of incident light, and, consequently, the absorption coefficient can be calculated by dividing the produced acoustic pressure by the light amount.

Figure 7:
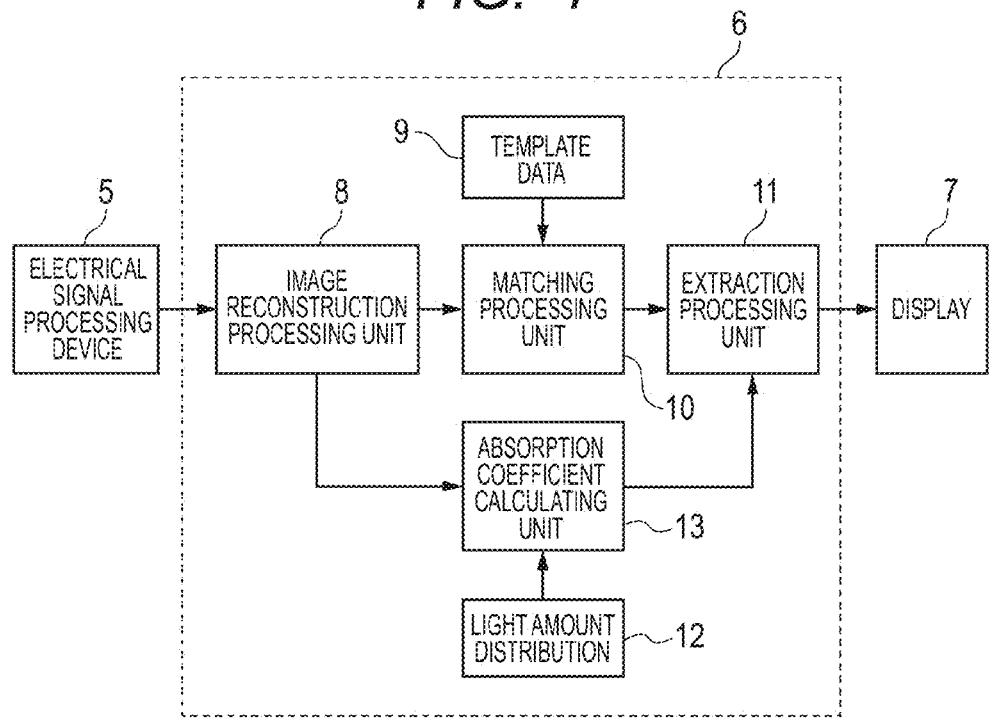
FIG. 7 is a schematic diagram illustrating a configuration of the device according to an embodiment of the present invention.

The entire device configuration according to the present embodiment is the same as in [Basic Embodiment], difference lies in the internal configuration of a data processing device 6. FIG. 7 illustrates an internal configuration of the data processing device 6 according to an embodiment which uses an absorption coefficient distribution for creating a similarity distribution. The absorption coefficient distribution is calculated by performing division in the absorption coefficient calculating unit 13 using the initial acoustic pressure distribution obtained from the image reconstruction processing unit 8 and a light amount distribution 12 calculated in advance. The light amount distribution 12 may be calculated by measuring a distribution of incident light per measurement. The matching processing unit 10 creates a similarity distribution according to matching processing using the initial acoustic pressure distribution and template data 9, the extraction processing unit 11 extracts the absorption coefficient distribution using the similarity distribution and the display 7 displays the absorption coefficient distribution. Although the embodiment has been described where processing up to extraction is performed, an embodiment is possible where only a similarity distribution is calculated as in [Basic Embodiment] and displayed.

Figure 8:
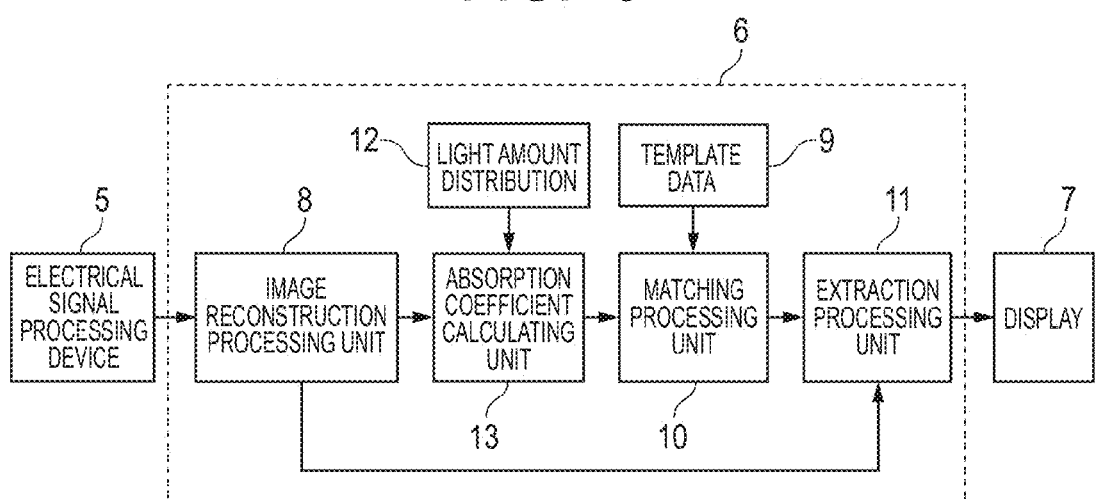
FIG. 8 is a schematic diagram illustrating a configuration of the device according to an embodiment of the present invention.
Figure 9:
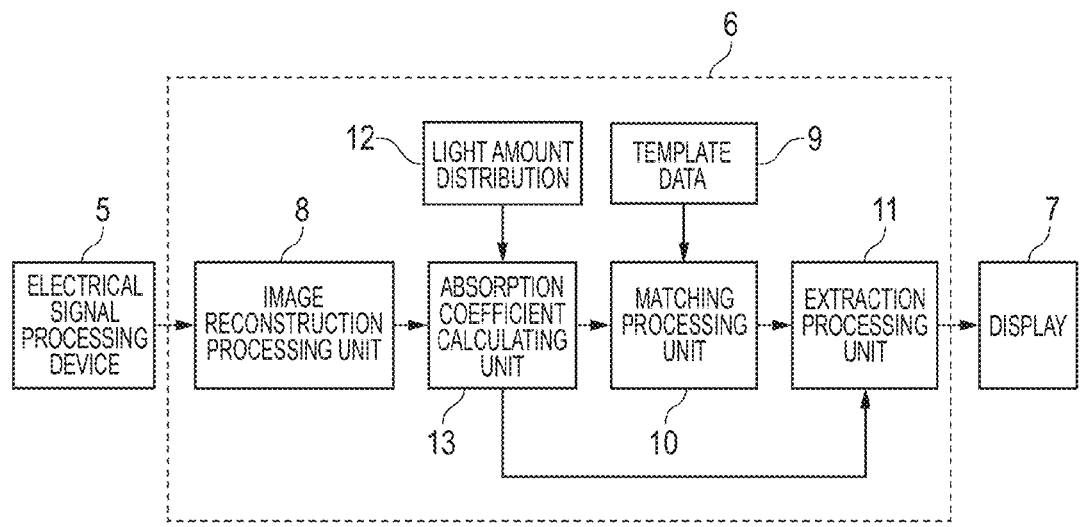
FIG. 9 is a schematic diagram illustrating a configuration of the device according to an embodiment of the present invention.

Further, other various combinations can be used for a distribution used for matching processing and extraction processing. FIG. 8 illustrates a device configuration according to an embodiment which creates a similarity distribution using the absorption coefficient distribution and extracts the initial acoustic pressure distribution. Further, FIG. 9 illustrates a device configuration according to an embodiment which creates the similarity distribution using the absorption coefficient distribution, and extracts the absorption coefficient distribution.

With the present embodiment, matching processing and extraction processing using the absorption coefficient distribution can be performed.

[Fourth Embodiment]

Figure 10:
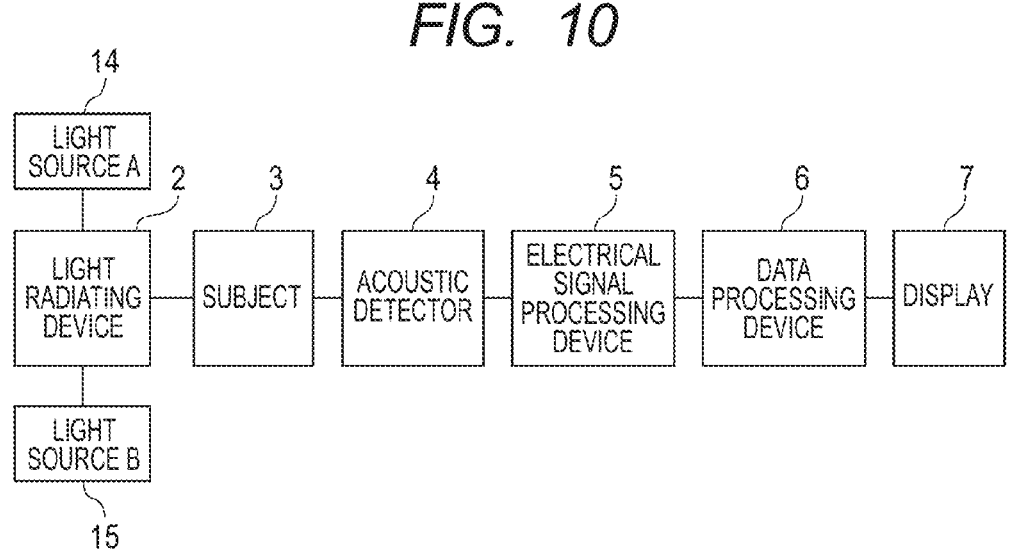
FIG. 10 is a schematic diagram illustrating a configuration of the device according to an embodiment of the present invention.

The embodiment will be described where the present invention is used to extract the concentration of oxygenated hemoglobin in all hemoglobin, that is, the oxygen saturation. As illustrated in FIG. 10, in the device configuration, a light source A 14 and a light source B 15 are arranged instead of the light source 1 of [Basic Embodiment]. The wavelengths of the light source A and light source B are different, and light is radiated at respectively different timings. Further, a light source C, a light source D and . . . having different wavelengths and timings may be added. By comparing the absorption coefficient distributions created by the respective light sources, it is possible to calculate an oxygen saturation distribution.

Figure 11:
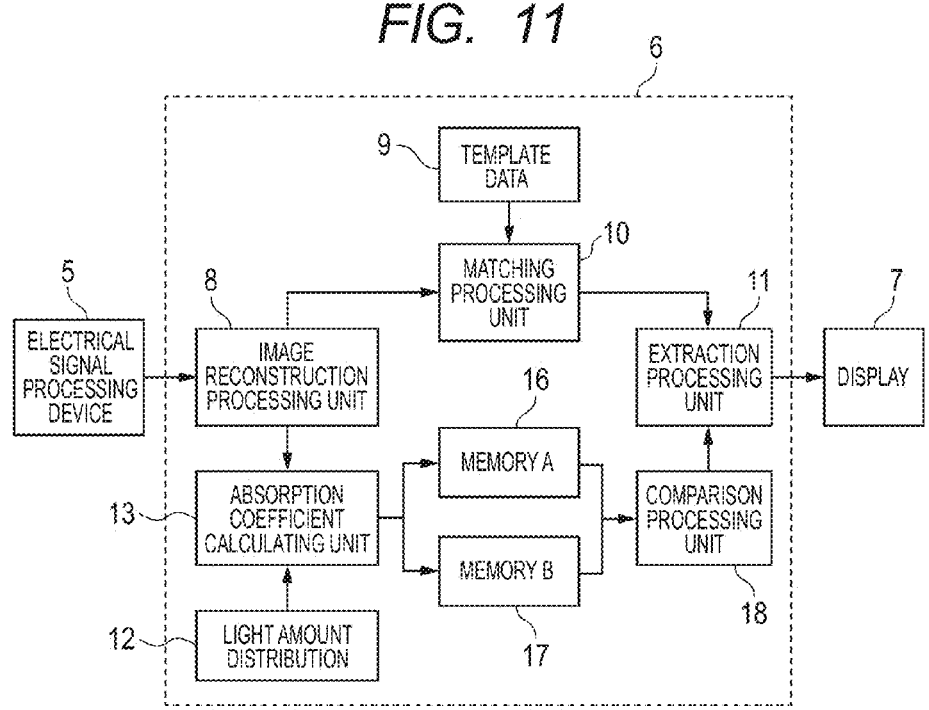
FIG. 11 is a schematic diagram illustrating a configuration of the device according to an embodiment of the present invention.

FIG. 11 is a view illustrating an internal configuration of a data processing device 6. An initial acoustic pressure distribution A created by the image reconstruction processing unit 8 from an acoustic wave from the light source A is converted into an absorption coefficient distribution A using the light among distribution 12 calculated in advance in the absorption coefficient calculating unit 13, and stored in a memory A 16. Further, concerning the light source B, an absorption coefficient distribution B obtained similarly is stored in a memory B 17. When more light sources are provided, respective absorption coefficient distributions are stored in a memory C, a memory D and . . . . Then, in the present embodiment, a comparison processing unit 18 which also serves as a concentration information calculating unit compares (described below) the absorption coefficient distribution A and absorption coefficient distribution B, and calculates the oxygen saturation distribution which is a concentration information distribution. On the other hand, the matching processing unit 10 matches the initial acoustic pressure distribution created by the image reconstruction processing unit 8 with template data 9, and creates a similarity distribution. The initial acoustic pressure distribution used in this case is desirably created using light sources of wavelengths having close absorption coefficients of both deoxygenated hemoglobin and oxygenated hemoglobin. In this case, matching processing may be performed using only the initial acoustic pressure distribution formed using one wavelength selected from the wavelengths used for measurement, or a plurality of initial acoustic pressure distributions obtained using a plurality of wavelengths may be matched and their results may be composed. Further, although it is desirable to use the initial acoustic pressure distribution for matching processing, the absorption coefficient distribution may be used. The extraction processing unit 11 extracts the oxygen saturation distribution using the similarity distribution, and outputs the result to the display 7.

The oxygen saturation is concentration information which can be calculated by comparing the absorption coefficient distributions created using light sources of different wavelengths. When mol absorption coefficients in blood are measured using lights having a wavelength $\lambda_1$ and wavelength $\lambda_2$, if absorptions of light by other than hemoglobin are assumed to be low in the wavelength $\lambda_1$ and wavelength $\lambda_2$ to such an extent that the absorptions can be ignored, the mol absorption coefficients $\mu_a(\lambda_1)[mm^{-1}]$ and $\mu_a(\lambda_2)[mm^{-1}]$ calculated when the wavelength $\lambda_1$ and wavelength $\lambda_2$ are used are represented by Equation 3 and Equation 4.

$$\mu_a(\lambda_1)=\epsilon_{ox}(\lambda_1)C_{ox}+\epsilon_{de}(\lambda_1)C_{de} \quad \text{Equation 3}$$

$$\mu_a(\lambda_2)=\epsilon_{ox}(\lambda_2)C_{ox}+\epsilon_{de}(\lambda_2)C_{de} \quad \text{Equation 4}$$

Meanwhile, $C_{ox}$ and $C_{de}$ refer to amounts (mol) of oxygenated hemoglobin and deoxygenated hemoglobin, and $\epsilon_{ox}(\lambda)$ and $\epsilon_{de}(\lambda)$ refer to mol absorption coefficients [mm$^{-1}$mol$^{-1}$] of oxygenated hemoglobin and deoxygenated hemoglobin at the wavelength $\lambda$, respectively. $\epsilon_{ox}(\lambda)$ and $\epsilon_{de}(\lambda)$ are obtained in advance by measurement or literature values, and simultaneous equations of Equations 3 and 4 are solved using measured values $\mu_a(\lambda_1)$ and $\mu_a(\lambda_2)$ to obtain $C_{ox}$ and $C_{de}$. When the number of light sources is great, the number of equations increases in proportion to the number of light sources, so that $C_{ox}$ and $C_{de}$ can be obtained by a least-square method. The oxygen saturation is defined at the ratio of oxygenated hemoglobin in all hemoglobin as in Equation 3, and can be calculated as in Equation 5, so that it is possible to obtain the oxygen saturation.

$$SO_2 = \frac{C_{ox}}{C_{ox} + C_{de}} \quad \text{Equation 5}$$

In the present embodiment, by extracting from the oxygen saturation distribution using the similarity distribution, it is possible to solve the problem that the image does not stand out in the oxygen saturation distribution. Further, although the abundance ratio of hemoglobin has been described with the present embodiment, according to the photoacoustic tomography, if an absorption spectrum is characteristic, the abundance ratio (concentration information distribution) other than hemoglobin can be calculated using the same principle and this abundance ratio may be extracted using the similarity distribution.

Further, similar to processing performed in FIGS. 8 and 9 in Third Embodiment, the similarity distribution may be found from the absorption coefficient distribution or oxygen saturation. Further, the initial acoustic pressure distribution or absorption coefficient distribution may be extracted from the obtained similarity distribution, and then the oxygen saturation distribution may be found from extracted data.

[Fifth Embodiment]

As described in [Basic Embodiment], the intensity ratio of an image and rearward artifact depends on the size of an optical absorber. Hence, the result of a similarity distribution becomes different depending on the size of the optical absorber used upon creation of template data, and a similarity close to the size of the optical absorber used upon creation of template data is highly evaluated. Hence, in the present embodiment, template data matching the sizes of a plurality of optical absorbers are prepared, and similarity distributions are created respectively and composed to create similarity distributions matching the sizes of various optical absorbers.

Figure 12:
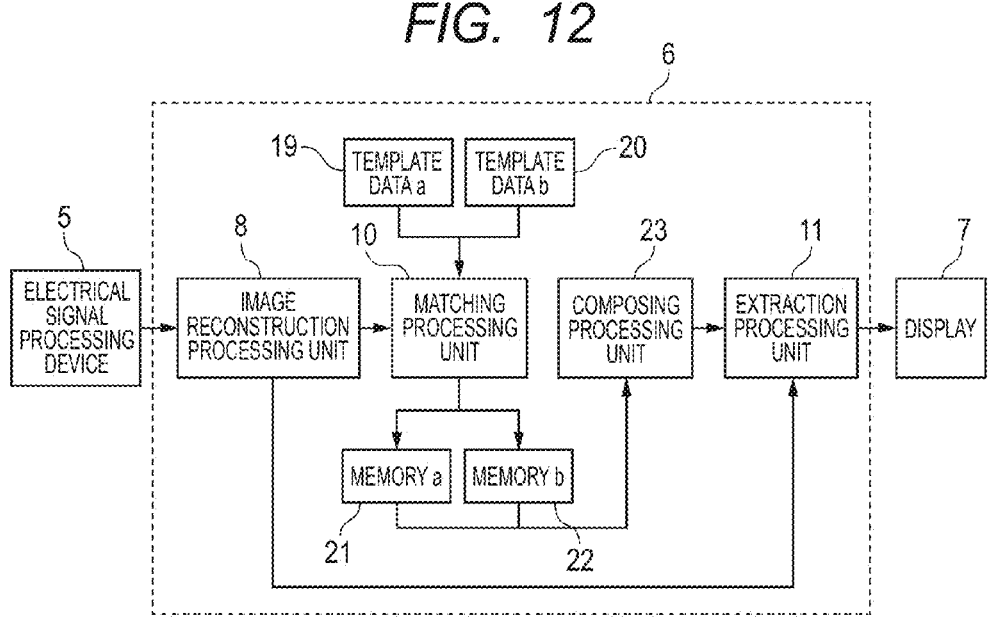
FIG. 12 is a schematic diagram illustrating a configuration of the device according to an embodiment of the present invention.

The entire device configuration is the same as in [Basic Embodiment], and the internal configuration of a data processing device 6 is different. FIG. 12 illustrates an internal configuration of the data processing device 6 according to the present embodiment. For template data, template data a 19 and template data b 20 are prepared. Those template data are each different in the size of an optical absorber upon simulation or actual measurement when data is created. While two types of template data are used herein, more types of template data may be used. The initial acoustic pressure distribution and each of template data a and template data b from the image reconstruction processing unit 8 are matched, and the created similarity distribution a and similarity distribution b are stored in a memory a 21 and memory b 22. Next, the composing processing unit 23 composes the similarity distribution a and similarity distribution b to create an integrated similarity distribution. To compose the similarity distributions, an average of the similarity distribution a and similarity distribution b is desirably found. However, a method of finding a square root of the product or a method of finding a root-mean-square may be adopted. Next, the initial acoustic pressure distribution created by the image reconstruction processing unit 8 is extracted using the integrated similarity distribution in the extraction processing unit 11, and the result is outputted to the display 7. These processings may not be limited to be performed only with respect to the initial acoustic pressure distribution, but can be performed with respect to the absorption coefficient distribution or oxygen saturation distribution. Further, after the extraction is performed, the absorption coefficient and oxygen saturation may be found, and outputted to the display 7.

In the present embodiment, the present invention can support optical absorbers of various sizes.

EXAMPLE 1

A result obtained when [Second Embodiment] is implemented in an experiment, and a result obtained using a conventional threshold method as a comparison example will be described. Cases where the used acoustic detectors have a limited frequency band are represented in examples 1-3.

A subject having a thickness of 50 mm, which was a simulated biological body in which an optical absorber was disposed at a position 25 mm from an acoustic detector, and of which optical characteristics and acoustic characteristics of a base material was made to match fat of the biological body. Inside the subject, three columnar optical absorbers having the diameter of 2 mm were laterally disposed, of which absorption coefficients were 20, 15 and 10 dB with respect to the base material. Polymethylpentene, as a subject holding plate, was closely attached to the face of the subject to be radiated by laser, and an acoustic detector was disposed across the polymethylpentene to dispose the subject, subject holding plate and acoustic detector in water. The acoustic detector was a 2D array acoustic detector having the frequency band at 1 MHz±40%, and array elements having the width of 2 mm were aligned as 23 elements in the longitudinal direction and 15 elements in the lateral direction, at the pitch of 2 mm. The subject was radiated by transmitting pulsed light having the wavelength of 1064 nm at the order of nanoseconds through water and polymethylpentene using Nd:YAG laser. The optical axis of incident light was aligned from normal line of the detection face of the acoustic detector, and light was radiated on the site of the subject on the front face of the acoustic detector. Pulsed light was radiated for 30 times, the resulting electrical signal was amplified and digital-to-analog converted, and finally digital signal was obtained. The sampling frequency of an analog/digital converter used in this case was 20 MHz and the resolution was 12 Bit. The digital signals of the respective elements were averaged and image reconstruction processing of the averaging result was performed to obtain an initial acoustic pressure distribution.

Figure 13A:
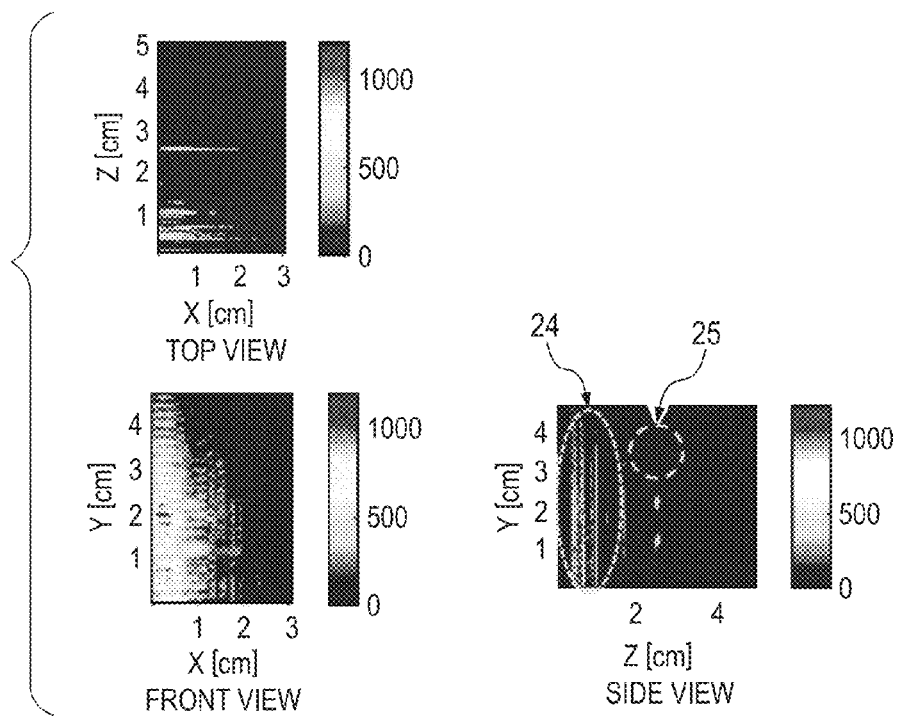
FIG. 13A illustrates an initial acoustic pressure distribution when the present invention is implemented in Example 1.

FIG. 13A illustrates the initial acoustic pressure distribution to which a conventional threshold method is applied. Display is provided in the Maximum Intensity Projection (MIP) format, and the direction seen from the acoustic detector was assumed as the front view and in a similar manner a side view and top view are also represented. The Z direction indicates a depth direction seen from the acoustic detector, and a numerical value of the Z axis becomes larger when it becomes further away from the acoustic detector, assuming the interface between the subject and subject holding plate as a zero point in the Z direction. The image indicated by a broken line circle 24 in the side view was noise produced when incident light reaches the surface of the acoustic detector and multiply reflected in the acoustic holding plate. Two images appearing below a broken line circle 25 represents optical absorbers of 20 and 15 dB or less. Although only voxels having values equal to or more than the threshold were displayed with the threshold method, since noise indicated by the broken line circle 24 had a greater intensity than the optical absorber positioned in the broken line circle 25, and therefore the optical absorber which should have been appeared there was removed while noise was left. Seen from the front view, since light was radiated from the left side, noise concentrated on the left side, and the columnar optical absorbers disposed in a direction along the X axis could not be seen at all due to the noise. Seen from the top view, although the columnar optical absorbers were seen at Z=2.5 cm, since light is weak on the right side, the intensity becomes weaker in the right side and the figure of the optical absorbers became less than the threshold and thereby the columnar optical absorber was removed.

Figure 13B:
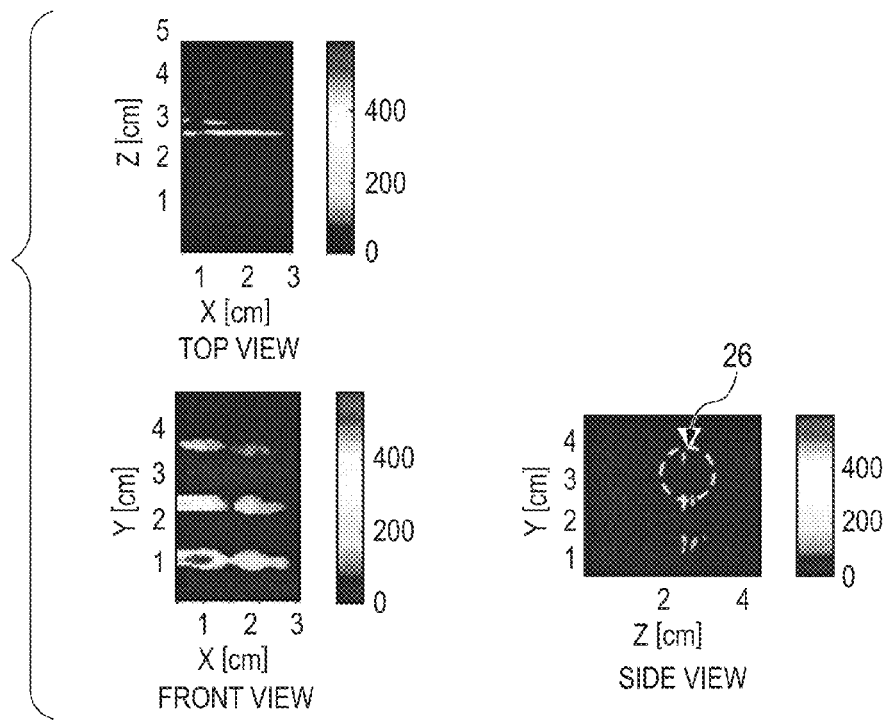
FIG. 13B illustrates an initial acoustic pressure distribution when a conventional method is implemented in Example 1.

FIG. 13B illustrates a result obtained by applying the present invention to the same data and extracting the initial acoustic pressure distribution based on the similarity distribution. The template data used at this time was created by simulation and includes an image of a ball having the diameter of 2 mm and a rearward artifact, and the similarity distribution was calculated according to ZNCC. Seen from the side view, since the noise portion had a low similarity with the template, the portion was not extracted, and the optical absorber of 10 dB indicated by a broken line circle 26 was extracted. Seeing the front view, noise could be removed, so that the images of the optical absorbers were clearly shown. Although the right side completely disappeared in the conventional threshold method, the images were extracted in the present method even on the right side on which light becomes weak.

This is because since normalization is performed in ZNCC, the similarity was determined based only on the relationship between an image and rearward artifact irrespective of the intensity of the distribution. As described above, only the image of the optical absorber could be extracted, which shows effectiveness of the present invention.

EXAMPLE 2

Figure 14A:
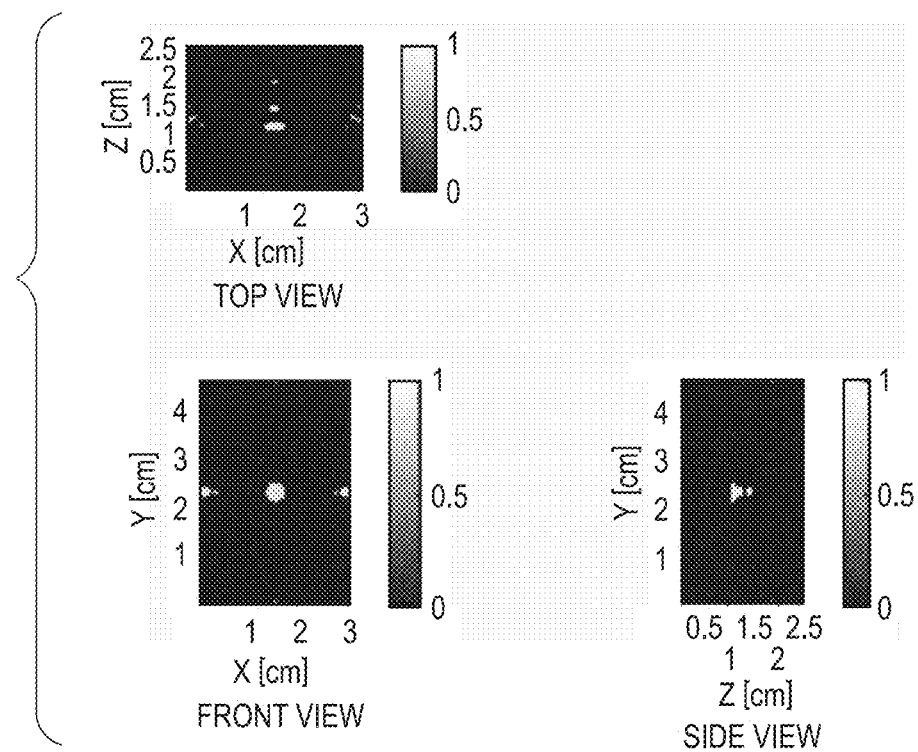
FIG. 14A illustrates an oxygen saturation distribution when the present invention is implemented in Example 2.
Figure 14B:
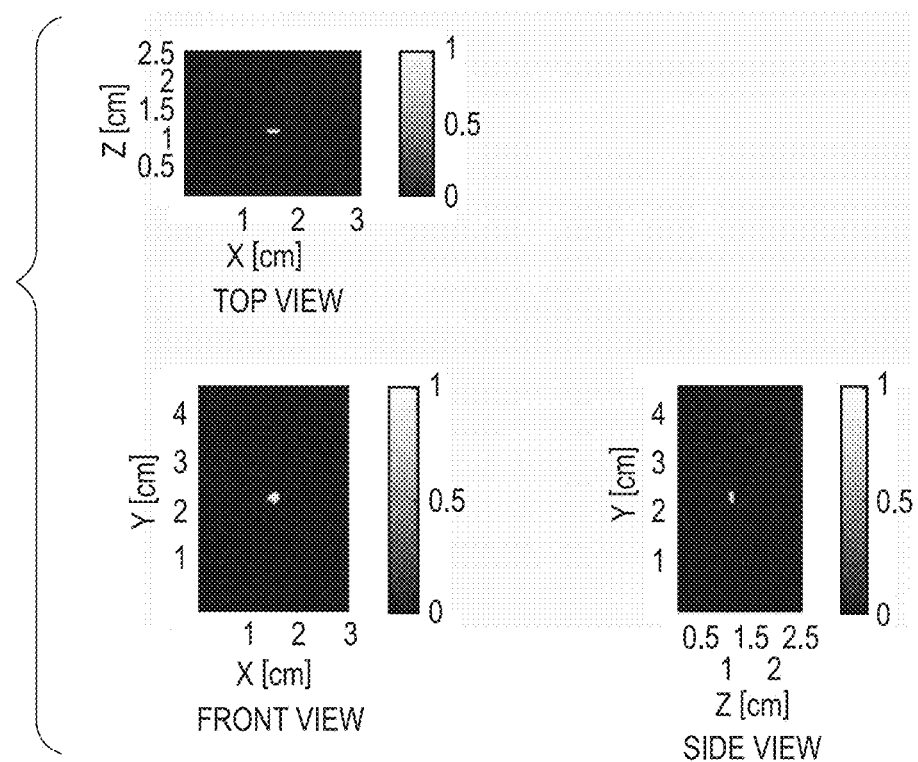
FIG. 14B illustrates an oxygen saturation distribution when the conventional method is implemented in Example 2.

FIGS. 14A and 14B illustrate a result obtained when [Fourth Embodiment] was implemented by simulation and a result obtained using a conventional threshold method as a comparison example. A signal at a position of the detector from a spherical acoustic source was simulated, and back projection was performed using this signal to obtain a result.

The detectors were set to have the same size, element pitch and frequency band as in [Example 1]. The acoustic velocity in the subject was 1500 m/s, an optical absorber was a ball having the diameter of 2 mm and obtained by mixing oxygenated hemoglobin and deoxygenated hemoglobin by 4 to 1. Pulsed lights having wavelengths of 756 nm and 825 nm was irradiated, and simulation and reconstruction were conducted per wavelength to obtain the initial acoustic pressure distribution. No noise was added in this case. For ease of description, it was assumed that light was not absorbed by a base material this time. By this means, it was possible to regard the light amount distribution to be constant, and to handle the initial acoustic pressure as the absorption coefficient distribution. Oxygen saturation distributions were derived from the absorption coefficient distribution of each wavelength according to Equations 3, 4 and 5.

FIG. 14A illustrates the initial acoustic pressure distribution to which a conventional threshold method was applied. FIG. 14A only illustrates an oxygen saturation distribution only for voxels having a higher intensity by providing a threshold which is 0.7 times as the maximum intensity in the absorption coefficient distribution. In the front view, the optical absorber disposed in the center indicates 0.8, that is, 80% of the oxygen saturation as predicted. However, artifacts stronger than the threshold were also produced on both sides and therefore these portions were also displayed. In the top view, there was further an artifact stronger than the threshold in the background of the optical absorber, and this portion was also displayed. In this way, there were cases where the conventional threshold method cannot completely remove a strong artifact even when a high contrast without noise can be realized.

FIG. 14B illustrates a result obtained by applying the present invention to the same data and extracting the oxygen saturation based on the similarity distribution. The template data used in this case was the same as in [Example 1], and the similarity distribution was calculated for an absorption coefficient distribution of 825 nm using NZCC.

In the front view, side view and top view, only the portion of the optical absorber was displayed at 80% of the oxygen saturation. As described above, the present invention is effective to calculate the oxygen saturation.

EXAMPLE 3

Figure 15A:
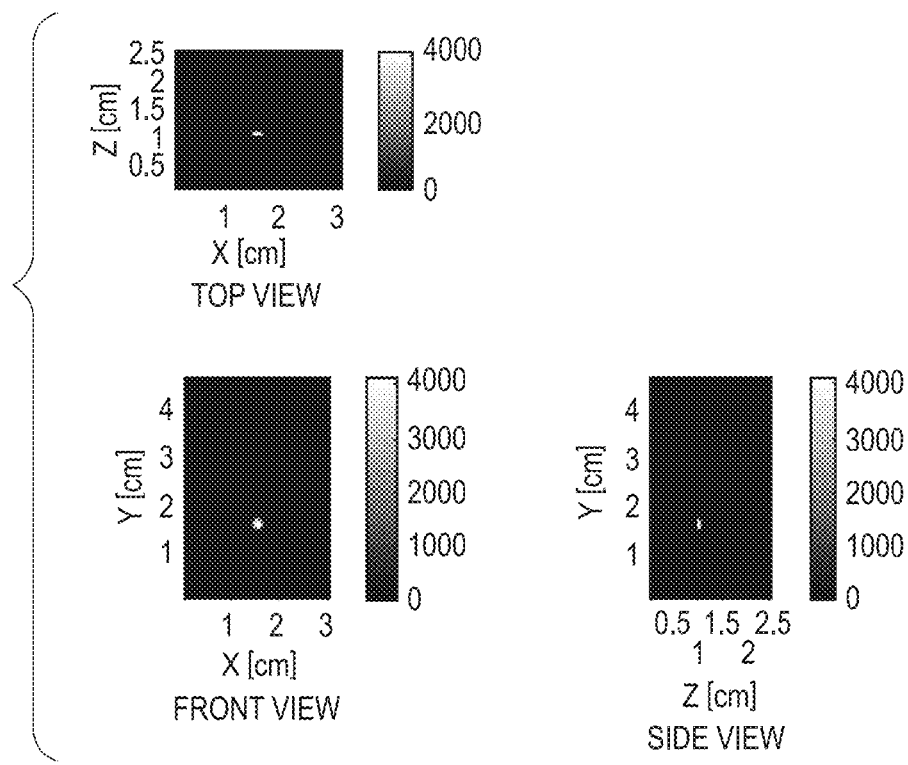
FIG. 15A illustrates an initial acoustic pressure distribution when a plurality of items of template data are used in Example 3.
Figure 15B:
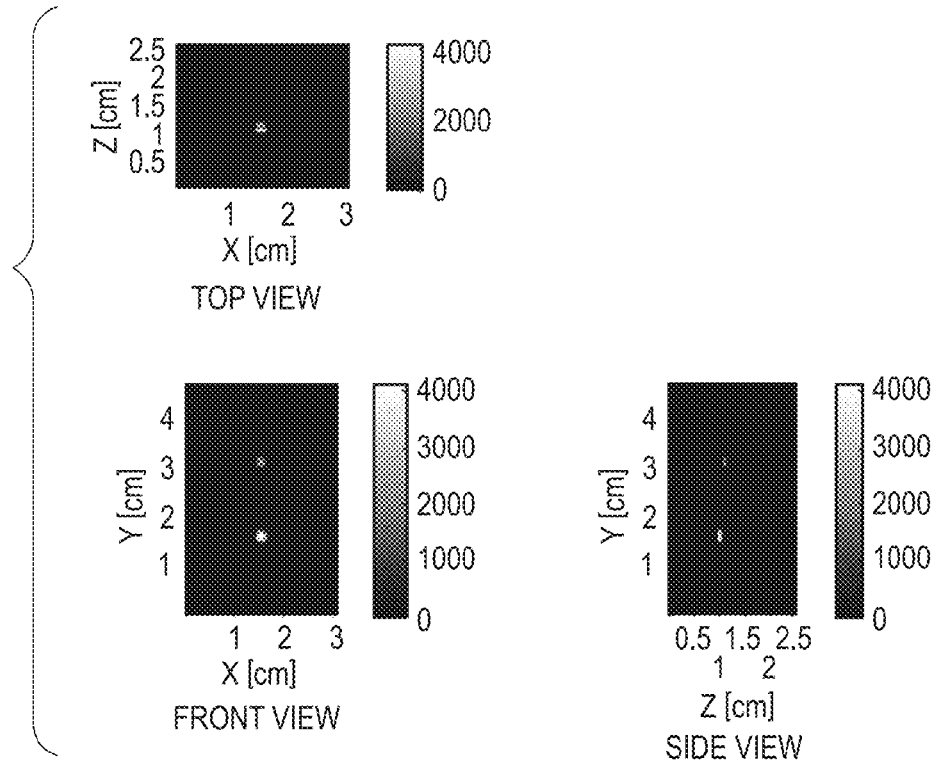
FIG. 15B illustrates an initial acoustic pressure distribution when one template is used in Example 3.

FIGS. 15A and 15B illustrates a result obtained when [Fifth Embodiment] was implemented by simulation, and a result obtained using only one template data as a comparison example. The simulation method was the same as in [Example 2].

The detectors were set to have the same size, element pitch and frequency band as in [Example 1]. The acoustic velocity in the subject was 1500 m/s, and optical absorbers were arranged as balls having the diameters of 2 mm and 4 mm by shifting their positions. The signal was acquired by simulation and reconstructed to obtain an initial acoustic pressure distribution of the matching target.

To create template data, the signal was acquired by simulating the optical absorber having the diameter of 4 mm and reconstructed to obtain the initial acoustic pressure distribution. This initial acoustic pressure distribution was 4 mm template data, and template matching was performed for the initial acoustic pressure distribution of the matching target to create a similarity distribution. FIG. 15A illustrates a result obtained by extracting the initial acoustic pressure distribution of the matching target based only on the similarity distribution created using this one template data. The optical absorber in the lower portion in the front view is a 4 mm ball, and since a 2 mm ball had a lower similarity, the smaller ball was not extracted.

An optical absorber having the diameter of 2 mm was further simulated to create template data and, similarly, 2 mm template data was acquired to obtain a similarity distribution. An average value of a similarity distribution using 4 mm template data and a similarity distribution using 2 mm template data was taken as an integrated similarity distribution. FIG. 15B illustrates a result obtained by extracting the initial acoustic pressure distribution of the matching target based on the integrated similarity distribution. Seen from the front view, a 4 mm optical absorber in the lower portion and a 2 mm optical absorber in the upper portion were displayed. As described above, the present invention is effective to support optical absorbers having various sizes by preparing a plurality of items of template data and integrating each similarity distribution.

EXAMPLE 4

In example 4, unlike the above examples, a case where the detector has a limited frequency band was compared to a case where the frequency band of the used detector is not limited. The simulation method was the same as in [Example 2].

Figure 16A:
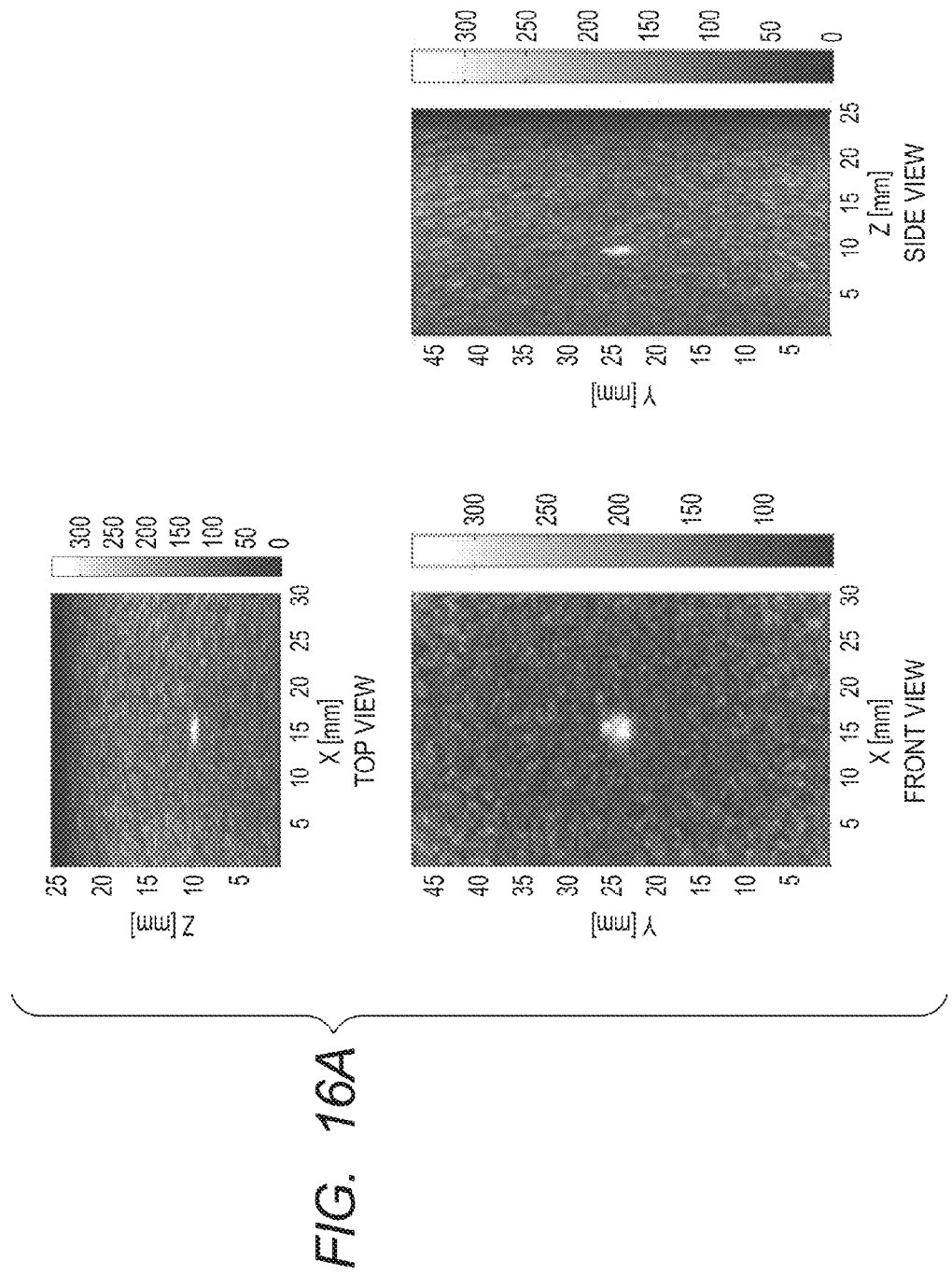
FIG. 16A is an initial acoustic pressure distribution when the whole frequency bands are detected and the conventional method is implemented in Example 4.

FIG. 16A illustrates the initial acoustic pressure distribution in a case where the frequency band of the used detector is not limited. The detectors were set to have the same size and element pitch as in [Example 1]. The condition was further set so that the optical absorber generates an acoustic wave of 320 Pa and the detectors can detect the whole frequency bands. The acoustic velocity in the subject was 1500 m/s, and an optical absorber was arranged as a ball having the diameter of 2 mm. The signal was acquired by simulation, and a random noise was applied to the obtained signal. The signal to which a noise of 20 Pa is applied was reconstructed to obtain an initial acoustic pressure distribution as illustrated in FIG. 16A.

Figure 16B:
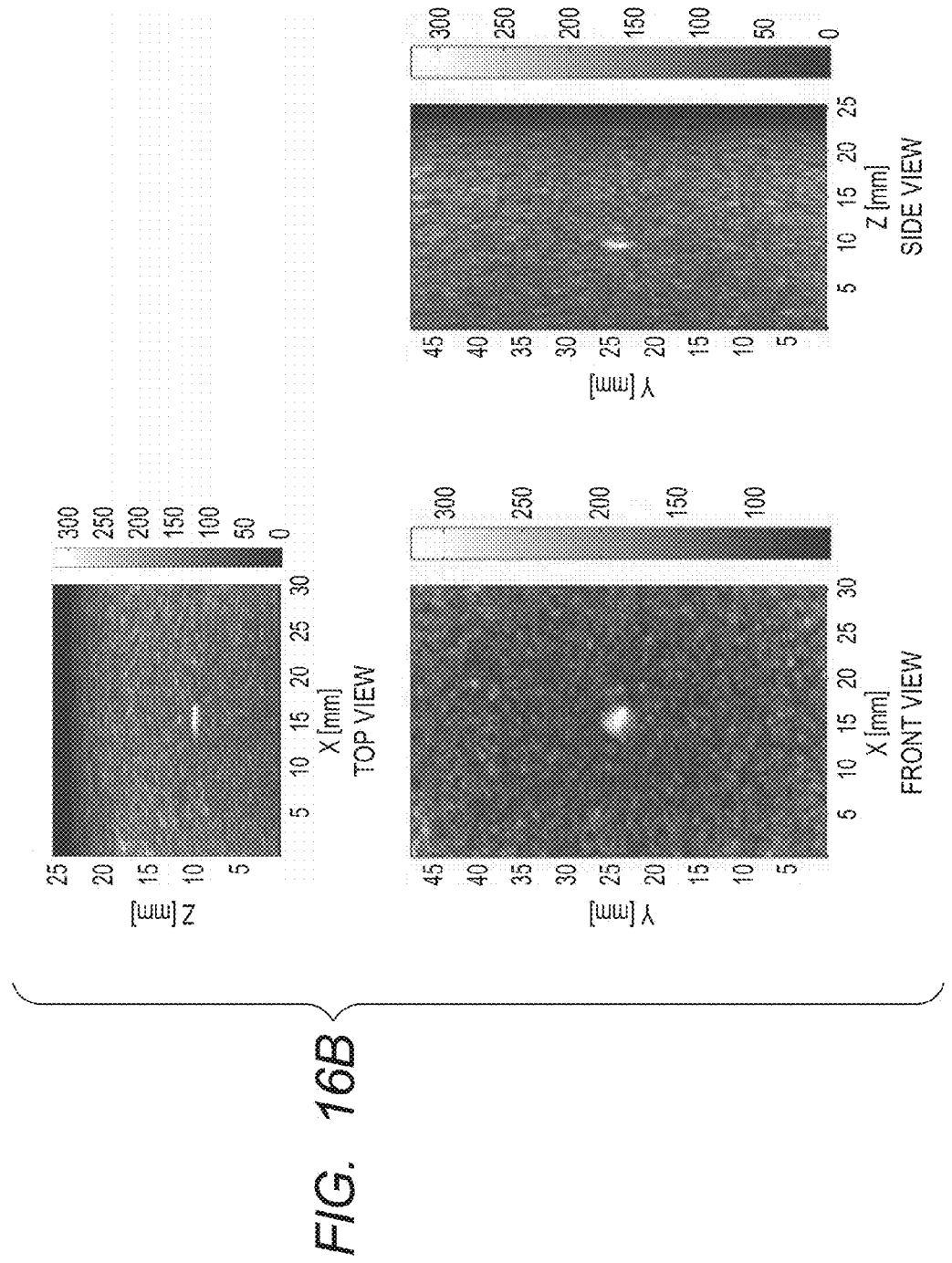
FIG. 16B is an initial acoustic pressure distribution when a limited frequency bands are detected and the conventional method is implemented in Example 4.

FIG. 16B illustrates the initial acoustic pressure distribution in a case where the used detector has a limited frequency band. To ensure the limited frequency band, the detector was set to have a normally-distributed frequency band at 1 MHz±40%. Other conditions were set to be the same as the prior simulation. A random noise having the same average intensity as of the prior simulation was applied to detected signal, and the signal to which the noise is applied was reconstructed to obtain an initial acoustic pressure distribution as illustrated in FIG. 16B.

As can be understood from FIGS. 16A and 16B, image contrast deteriorated due to noise, irrespective of whether or not the frequency band is limited, and the image of the optical absorber could hardly be discriminated.

Figure 16C:
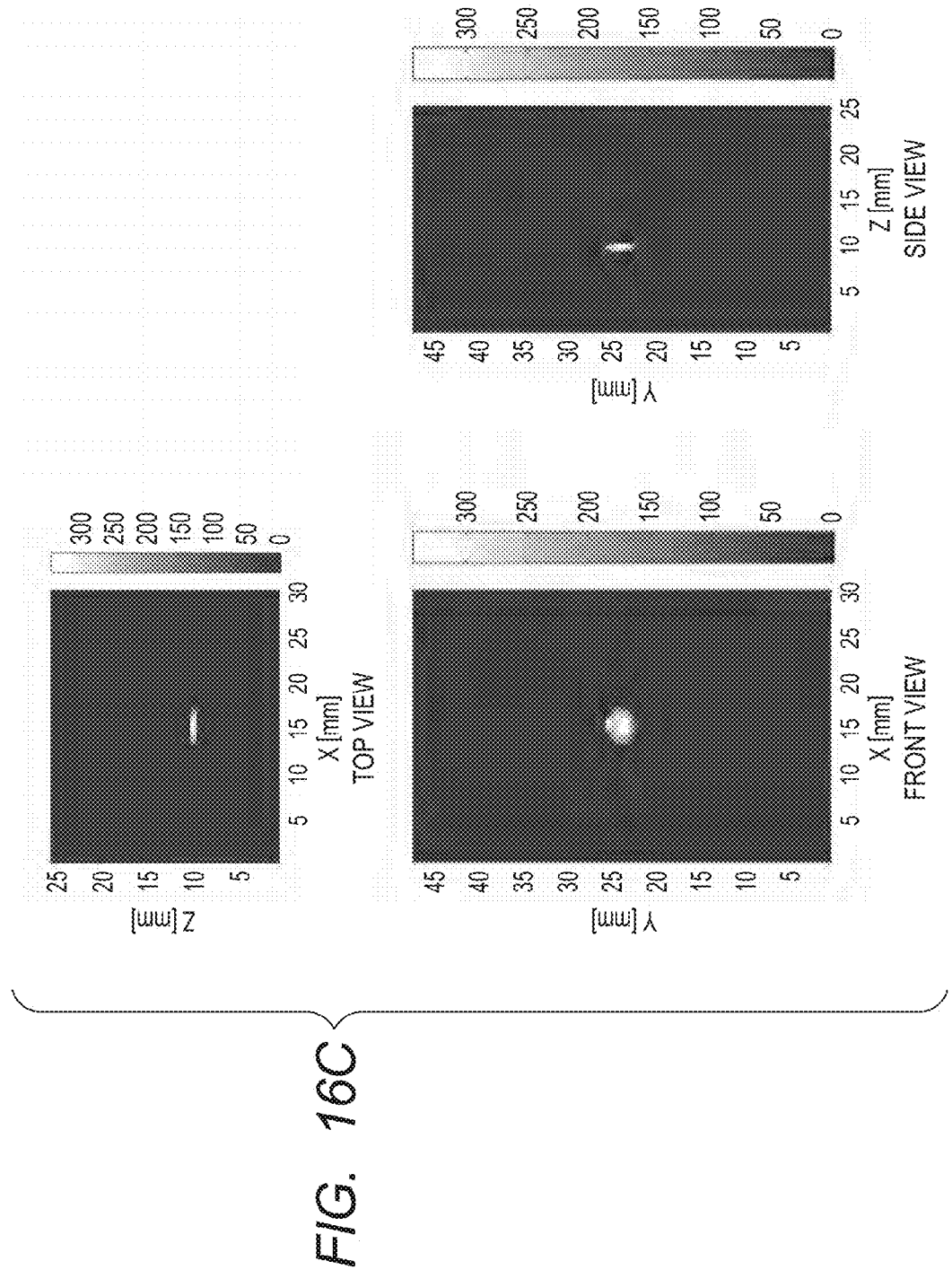
FIG. 16C is an initial acoustic pressure distribution when the whole frequency bands are detected and the present invention is implemented in Example 4.
Figure 16D:
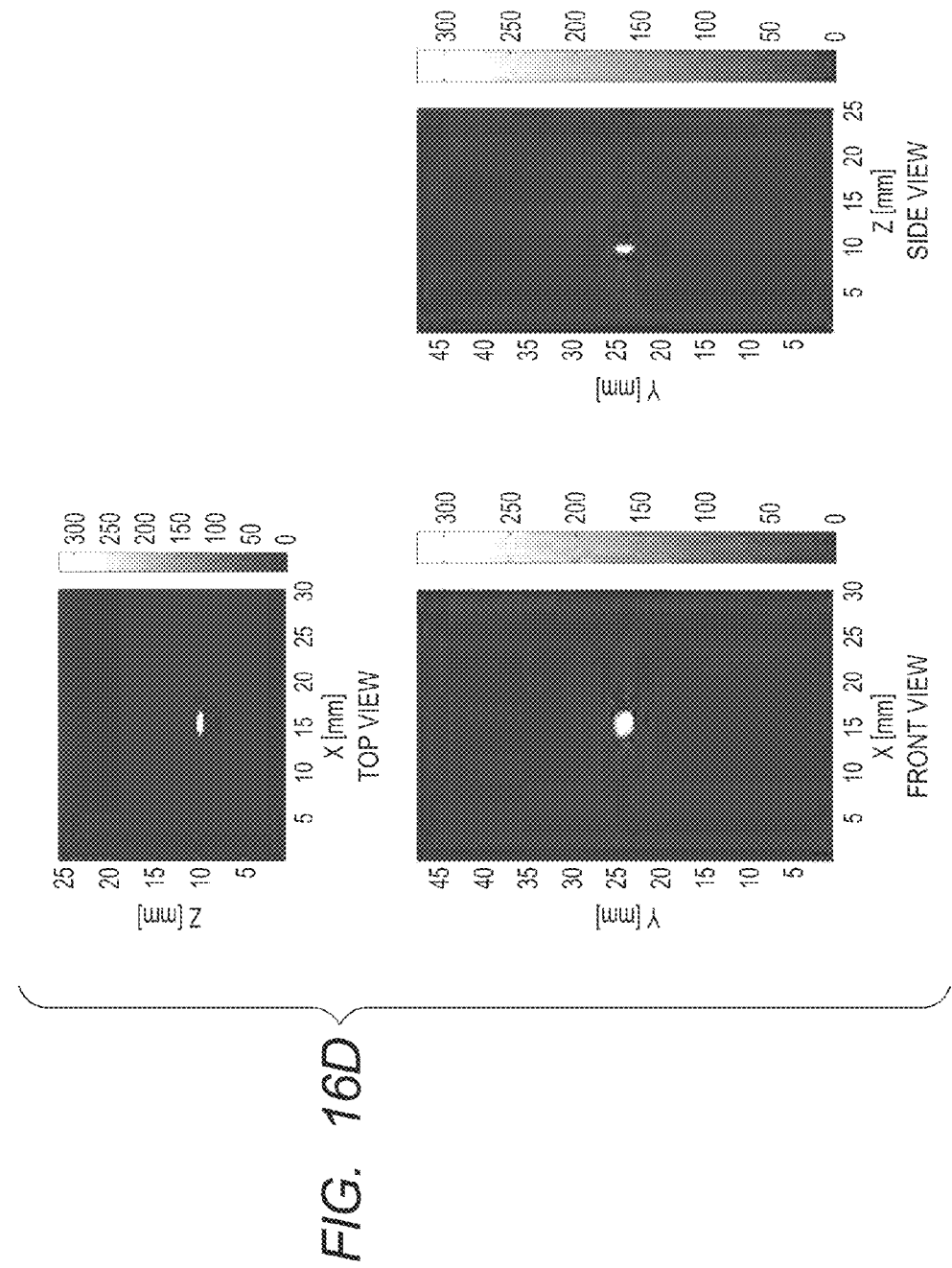
FIG. 16D is an initial acoustic pressure distribution when a limited frequency bands are detected and the present invention is implemented in Example 4.

Then, an optical absorber having the diameter of 2 mm was further simulated in each conditions of detecting the whole frequency bands and detecting a limited frequency bands at 1 MHz±40% to, obtain signals, reconstruct the signals and create initial acoustic pressure distributions, which are used as template data of each conditions. Template matching was independently performed for initial acoustic pressure distributions of the matching target to create similarity distributions, and images were extracted from the initial acoustic pressure distributions of the matching target based on the created similarity distributions FIG. 16C illustrates the extracted result of the case where the frequency band of the used detector is not limited, and FIG. 16D illustrates the extracted result of the case where the used detector has a limited frequency band. In the case where the frequency band of the used detector is not limited, negative artifacts appeared back and forth of a real image were used for template matching. In the case where the used detector has a limited frequency band, a rearward artifact due to ringing is further added for template matching. Thus the accuracy of the similarity distribution is enhanced in the case where the used detector has a limited frequency band, which causes the difference of the extracted region between FIGS. 16C and 16D. The difference of the absolute value of the extracted region may be due to an attenuation of the signal due to limitation of the frequency bands and the randomness of the noise. In FIGS. 16C and 16D, since the optical absorber is extracted as above, and the contrast of the image is enhanced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-288685, filed on Dec. 24, 2010 which is hereby incorporated by reference herein in its entirety.

REFERENCE SIGNS LIST

1 LIGHT SOURCE
2 LIGHT RADIATING DEVICE
3 SUBJECT
4 ACOUSTIC DETECTOR
5 ELECTRICAL SIGNAL PROCESSING DEVICE
6 DATA PROCESSING DEVICE
7 DISPLAY
8 IMAGE RECONSTRUCTION PROCESSING UNIT
9 TEMPLATE DATA
10 MATCHING PROCESSING UNIT
11 EXTRACTION PROCESSING UNIT
12 LIGHT AMOUNT DISTRIBUTION
13 ABSORPTION COEFFICIENT CALCULATING UNIT
14 LIGHT SOURCE A
15 LIGHT SOURCE B
16 MEMORY A
17 MEMORY B
18 COMPARISON PROCESSING UNIT
19 TEMPLATE DATA a
20 TEMPLATE DATA b
21 MEMORY a
22 MEMORY b
23 COMPOSITION PROCESSING UNIT
24 BROKEN LINE CIRCLE INDICATING NOISE PORTION
25 BROKEN LINE CIRCLE INDICATING POSITION OF OPTICAL ABSORBER OF 10 dB
26 BROKEN LINE CIRCLE INDICATING POSITION OF OPTICAL ABSORBER OF 10 dB

The invention claimed is:

1. A subject information acquiring device comprising:
   an acoustic detector configured to convert an acoustic wave propagated in a subject into an electrical signal; and
   a data processing unit configured to acquire a subject information distribution as pixel or voxel data using the electrical signal,
   wherein said data processing unit holds a plurality of items of template data, each item indicating a relationship between a real image and an artifact which is a virtual image accompanying the real image, the plurality of items being different from each other,
   wherein said data processing unit is configured to calculate a plurality of similarities respectively between the plurality of items of template data and the subject information distribution,
   wherein said data processing unit is configured to acquire an integrated similarity distribution using the plurality of similarities, and
   wherein the plurality of items of template data correspond respectively to optical absorbers of different sizes.

2. The subject information acquiring device according to claim 1, wherein said data processing unit is configured to determine a site, in the integrated similarity distribution, including a higher similarity than a threshold, and
   wherein said data processing unit is configured to cause a display unit to display the subject information distribution at the determined site.

3. The subject information acquiring device according to claim 1, wherein said data processing unit is configured to acquire an initial acoustic pressure distribution as the subject information distribution.

4. The subject information acquiring device according to claim 1, wherein the acoustic wave is generated by light irradiation of the object, and wherein said data processing unit is configured to acquire an initial acoustic pressure distribution using the electrical signal and acquire an absorption coefficient distribution as the subject information distribution using a light amount distribution in the subject and the initial acoustic pressure distribution.

5. The subject information acquiring device according to claim 1, wherein the acoustic wave includes a plurality of acoustic waves generated by irradiation of the subject with a plurality of pulsed lights including respectively different wavelengths,
   wherein said acoustic detector is configured to convert the plurality of acoustic waves into a plurality of electrical signals, and
   wherein said data processing unit is configured to acquire a concentration information distribution as the subject information distribution using the plurality of electrical signals.

6. The subject information acquiring device according to claim 1, wherein the artifact is one that appears when only a part of acoustic wave propagated in a specific direction, among whole generated acoustic waves, is detected.

7. The subject information acquiring device according to claim 1, wherein the artifact is one that is caused by response characteristics of said acoustic detector.

8. A subject information acquiring device comprising:
an acoustic detector configured to convert an acoustic wave propagated in a subject into an electrical signal; and
a data processing unit which holds a plurality of items of template data, each item indicating a relationship between a real image and an artifact which is a virtual image accompanying the real image, the plurality of items being different from each other,
wherein said data processing unit is configured to:
acquire a first subject information distribution as pixel or voxel data using the electrical signal,
calculate a plurality of similarities respectively between the plurality of items of template data and the first subject information distribution,
acquire an integrated similarity distribution using the plurality of similarities,
determine a site, in the integrated similarity distribution, including a higher similarity than a threshold, and
acquire a second subject information distribution of a type different from the first subject information distribution at the site, as pixel or voxel data, using the electrical signal, and
wherein the plurality of items of template data correspond respectively to optical absorbers of different sizes.

9. The subject information acquiring device according to claim 8, wherein the acoustic wave includes a plurality of acoustic waves generated by irradiation of the subject with a plurality of pulsed lights including respectively different wavelengths,
wherein said acoustic detector is configured to convert the plurality of acoustic waves into a plurality of electrical signals, and
wherein said data processing unit is configured to:
acquire the first subject information distribution using at least one of the plurality of electrical signals, and
acquire a concentration information distribution as the second subject information distribution using the plurality of electrical signals.

10. The subject information acquiring device according to claim 9, wherein said data processing unit is configured to acquire an oxygen saturation distribution as the concentration information distribution.

11. The subject information acquiring device according to claim 8, wherein said data processing unit is configured to acquire an initial acoustic pressure distribution or an absorption coefficient distribution as the first subject information distribution.

12. The subject information acquiring device according to claim 8, wherein said data processing unit is configured to cause a display unit to display the second subject information distribution at the site.

13. The subject information acquiring device according to claim 1, wherein said acoustic detector includes a transducer comprising a piezoelectric material.

14. The subject information acquiring device according to claim 8, wherein said acoustic detector includes a transducer comprising a piezoelectric material.

15. The subject information acquiring device according to claim 1, wherein said data processing unit is configured to acquire the integrated similarity distribution by averaging the plurality of similarities.

16. The subject information acquiring device according to claim 1, wherein said data processing unit is configured to acquire the integrated similarity distribution by calculating a square root of a product of the plurality of similarities.

17. The subject information acquiring device according to claim 1, wherein said data processing unit is configured to acquire the integrated similarity distribution by calculating a root-mean-square of the plurality of similarities.

18. The subject information acquiring device according to claim 1, wherein the acoustic wave includes a plurality of acoustic waves generated by irradiation of the subject with a plurality of pulsed lights including respectively different wavelengths.

19. The subject information acquiring device according to claim 8, wherein the acoustic wave includes a plurality of acoustic waves generated by irradiation of the subject with a plurality of pulsed lights including respectively different wavelengths.

20. The subject information acquiring device according to claim 1, wherein said data processing unit is configured to cause a display unit to display the integrated similarity distribution.

21. The subject information acquiring device according to claim 8, wherein said data processing unit is configured to cause a display unit to display the integrated similarity distribution.

* * * * *